US009422521B2

(12) United States Patent  
Davidson et al.

(10) Patent No.: US 9,422,521 B2  
(45) Date of Patent: Aug. 23, 2016

(54) DIFFERENTIATION OF PLURIPOTENT STEM CELLS WITH A KINASE INHIBITOR OR PGI2

(75) Inventors: Bruce Paul Davidson, Singapore (SG); Ralph Eberard Graichen, Singapore (SG); Robert Zweigerdt, Singapore (SG); Xiuqin Xu, Singapore (SG)

(73) Assignee: ES Cell International Pte Ltd., Alameda, CA (US)

( * ) Notice: Subject to any disclaimer, the term of this patent is extended or adjusted under 35 U.S.C. 154(b) by 2366 days.

(21) Appl. No.: 12/066,624

(22) PCT Filed: Sep. 12, 2006

(86) PCT No.: PCT/AU2006/001333  
§ 371 (c)(1), (2), (4) Date: Apr. 8, 2008

(87) PCT Pub. No.: WO2007/030870  
PCT Pub. Date: Mar. 22, 2007

(65) Prior Publication Data  
US 2008/0187494 A1    Aug. 7, 2008

Related U.S. Application Data

(60) Provisional application No. 60/716,390, filed on Sep. 12, 2005, provisional application No. 60/740,462, filed on Nov. 29, 2005, provisional application No. 60/753,434, filed on Dec. 22, 2005.

(51) Int. Cl.
| | |
|---|---|
| *C12N 5/0735* | (2010.01) |
| *C12N 5/073* | (2010.01) |
| *C12N 5/0797* | (2010.01) |
| *C12N 5/077* | (2010.01) |
| *A61K 35/12* | (2015.01) |

(52) U.S. Cl.  
CPC ........... *C12N 5/0606* (2013.01); *C12N 5/0603* (2013.01); *C12N 5/0623* (2013.01); *C12N 5/0657* (2013.01); *A61K 35/12* (2013.01); *C12N 2500/24* (2013.01); *C12N 2500/38* (2013.01); *C12N 2500/90* (2013.01); *C12N 2501/02* (2013.01); *C12N 2501/115* (2013.01); *C12N 2501/155* (2013.01); *C12N 2501/385* (2013.01); *C12N 2501/727* (2013.01); *C12N 2501/999* (2013.01); *C12N 2502/02* (2013.01); *C12N 2502/13* (2013.01); *C12N 2503/02* (2013.01); *C12N 2506/02* (2013.01)

(58) Field of Classification Search  
None  
See application file for complete search history.

(56) References Cited

U.S. PATENT DOCUMENTS

2006/0069018 A1 *   3/2006   Sakai et al. ..................... 514/12

FOREIGN PATENT DOCUMENTS

WO    WO 03/093487 A1    11/2003  
WO    2006066320          6/2006

OTHER PUBLICATIONS

Examination Report corresponding to UK Patent Application No. 0806557.5, dated Oct. 12, 2009.  
Schulz T.C. et al., "Differentiation of human embryonic stem cells to dopaminergic neurons in serum-free suspension culture", Stem Cells 22:1218-1238 (2004).  
Liour, S.S. et al. "Differentiation of Radial Glia From Embryonic Stem Cells in Chemically Defined Medium", Program No. 564.5 2003, Abstract Viewer/Itinerary Planner. Washington D.C.: Society for Neuroscience (2003) Online.  
Johansson, B.M. et al., "Evidence for Involvement of Activin A and Bone Morphogenetic Protein 4 in Mammaliam Mesoderm and Hematopoietic Development", Molecular and Cellular Biology 15(1):141-151 (1995).  
Wiles M. V. et al., "Analysis of Factors Controlling Primary Germ Layer Formation and Early Hematopoiesis Using Embroyonic Stem Cell In Vitro Differentiation", Lukemia Suppl 3:454-456 (1997).  
Wiles M. V. et al., "Embryonic Stem Cell Development in a Chemically Defined Medium", Experimental Cell Research 247:241-248 (1999).  
Honda M. et al., "RXR agonist enhances the differentiation of cardiomyocytes derived from embryonic stem cells in serum-free conditions" Biochemical and Biophysical Research Communications 333:1334-1340 (2005).  
Sachinidis A. et al., "Identification of Plateled-derived Growth Factor-BB as Cardiogenesis-Inducing Factor in Mouse Embryonic stem cells under Serum-free Conditions" Cellular Physiology and Biochemistry 13:423-429 (2003).  
Bouhon I. A. et al., "Neural differentiation of mouse embryonic stem cells in chemically defined medium", Brain Research Bulletin 68:62-75 (2005).  
Passier R. et al., "Increased Cardiomyocyte Differentiation from Human Embryonic Stem Cells in Serum-Free Cultures", Stem Cells 23:772-780 (2005).  
Engel F. B. et al., "p38 MAP kinase inhibition enables proliferation of adult mammalian cardiomyocytes", Genes & Development 19:1175-1187 (2005).  
Yoshida, et al. Journal of Cell Science 111:769, Cell Heterogeneity Upon Myogenic Differentiation: Down Regulation of MyoD and Myf-5 Generates Reserve Cells.

* cited by examiner

*Primary Examiner* — Blaine Lankford  
(74) *Attorney, Agent, or Firm* — E. Stewart Mittler; Krista P. Kauppinen

(57) ABSTRACT

The present invention provides a process of differentiating stem cells, in particular hES cells, into cardiomyocytes and into neural progenitors by growing the hES cells in the presence of a defined medium that is substantially free of xeno- and serum-components and thus comprises a clinically compliant medium. The defined media comprises defined factors that contribute to the promotion of differentiation to cardiomyocytes and neural progenitors. The invention also includes defined culture media and cell populations and methods of using them.

15 Claims, 29 Drawing Sheets

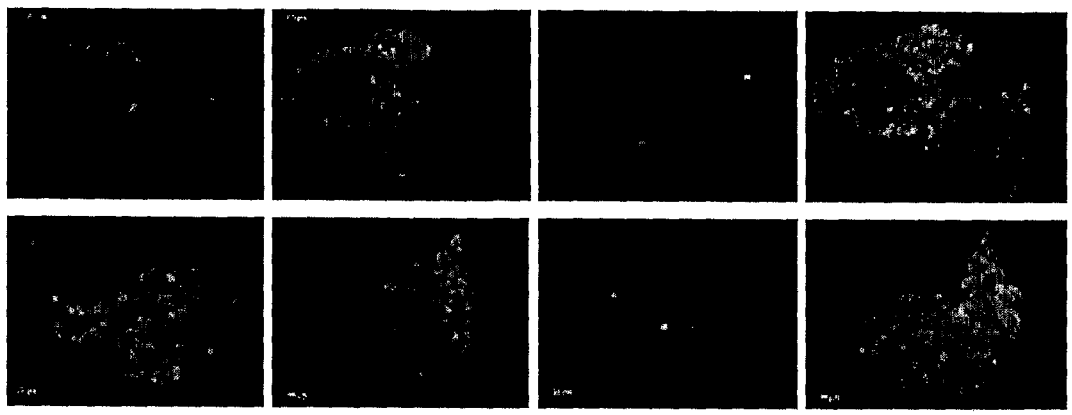
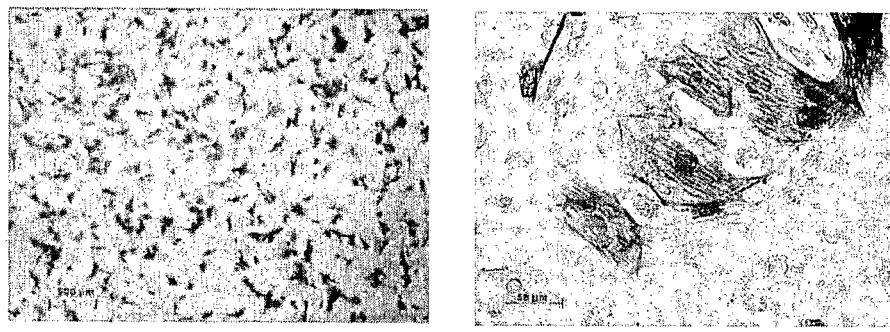
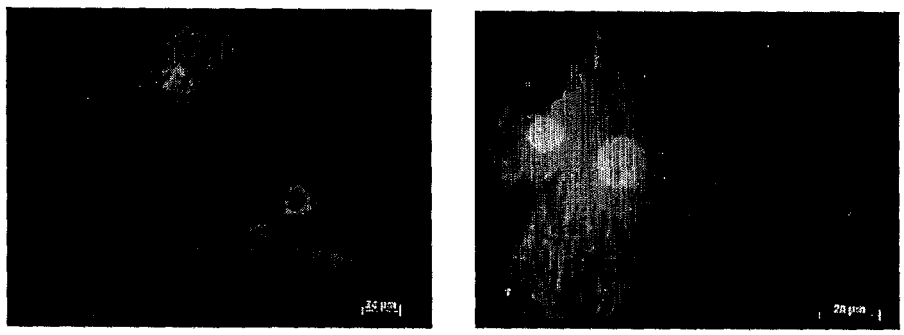
FIG 17

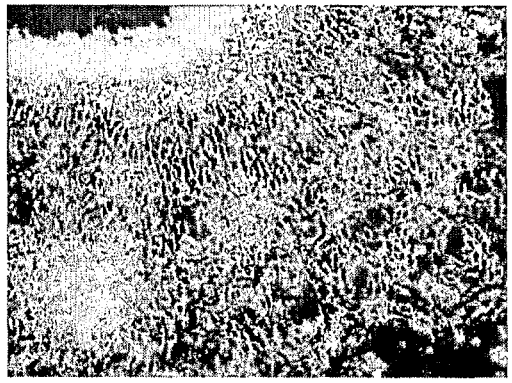
FIG 23

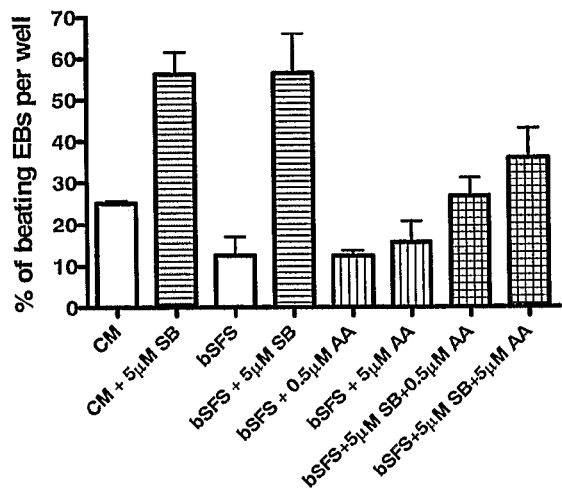
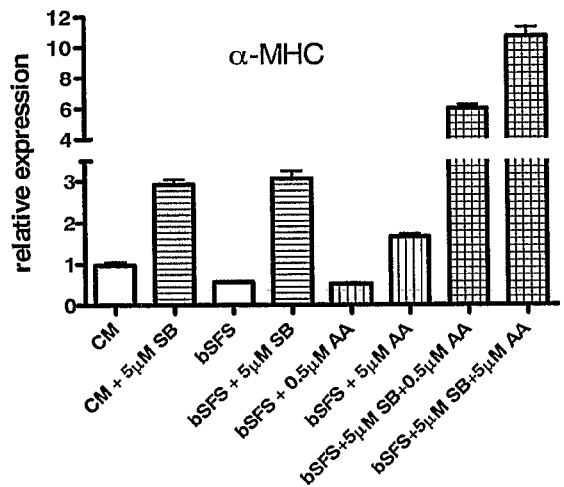
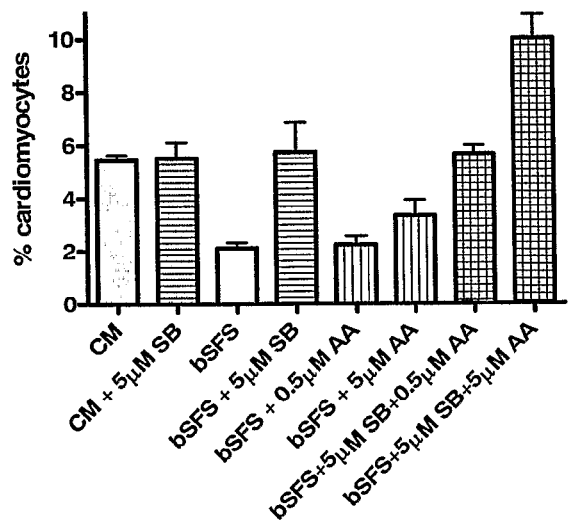
FIG 25

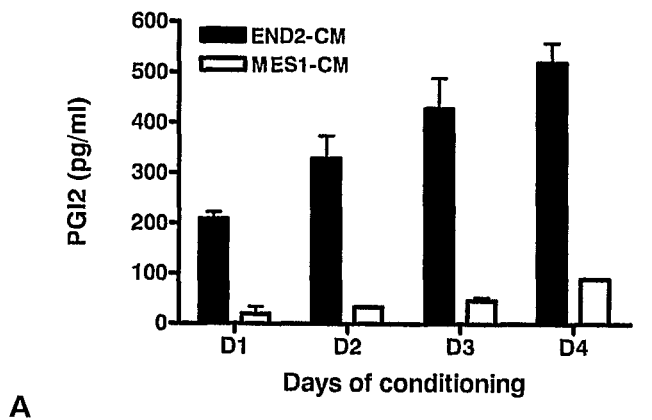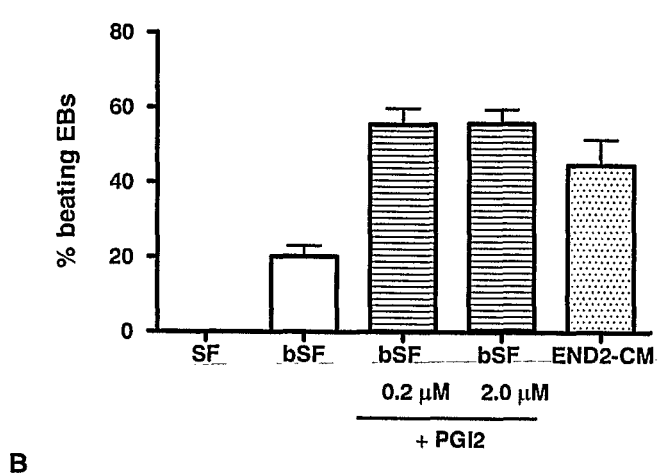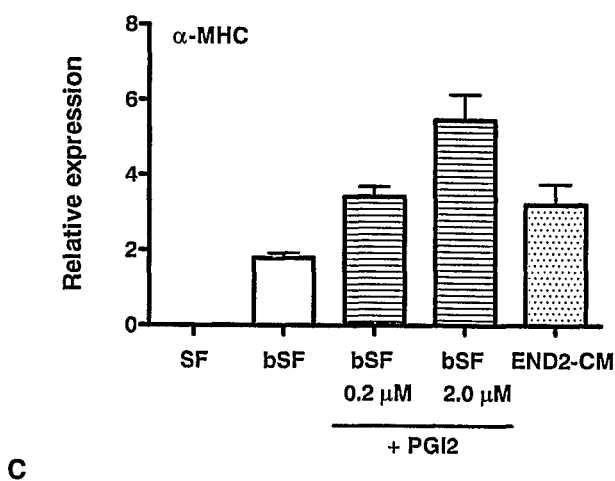
FIG 28

DIFFERENTIATION OF PLURIPOTENT STEM CELLS WITH A KINASE INHIBITOR OR PGI2

CROSS-REFERENCE TO RELATED APPLICATIONS

This application is a national stage entry of PCT/AU2006/001333, filed on Sep. 12, 2006, which claims priority to U.S. provisional application Nos. 60/753,434, filed Dec. 22, 2005, 60/740,462, filed Nov. 29, 2005, and 60/716,390, filed Sep. 12, 2005, all of which are incorporated by reference in their entireties.

FIELD OF THE INVENTION

The present invention relates to a process and composition for controlling germ layer differentiation preferably from human embryonic stem (hES) cells and promoting mesoderm formation and cardiomyogenesis from hES cells or other stem cell (SC) types.

BACKGROUND OF THE INVENTION

Cardiomyocyte differentiation in embryonic stem cells is poorly defined and a relatively nonselective process. hES cells and mouse embryonic stem (mES) cells have intrinsic differences in their response to biochemical factors (1). Consistent with these observations is the finding that cardiomyocyte differentiation between human ES cells or mouse ES cells or embryonic carcinoma (EC) cells is indeed dissimilar (2).

Differentiation of mouse embryonic stem cells into cardiomyocytes has historically been achieved through spontaneous differentiation in serum-containing medium or through treatment with compounds like DMSO, retinoic acid, Bone morphogenetic proteins, Fibroblast growth factors or the broad and non-specific de-methylating agent 5-aza-deoxycytidine (3,4). Compounds such as 5-aza-deoxycytidine have also been used to induce differentiation of cardiomyocytes from other stem cell types (adult bone marrow or fat tissue (5,6)). This indicates that different types of stem cells could potentially be used as a source for the generation of cardiomyocytes for applications such as cell therapy, tissue engineering, pharmacological and toxicological screening, or etc, provided effective processes and methods for the derivation of cardiomyocyte are available.

Current published methods for forming cardiomyocytes from hES cells rely on spontaneous differentiation in media containing animal serum (e.g. fetal bovine serum or calf serum), a media component that is largely undefined and subject to batch-to-batch variations. An enhancement of cardiomyocyte differentiation under these conditions can be achieved by treatment with 5-aza-2'-deoxycytidine (7). The differences between mouse and human ES cells is exemplified by the observation that the addition of DMSO or retinoic acid has no detectable effect on cardiomyogenesis when hES cells are treated although these compounds have shown an inductive effect on cardiomyocyte differentiation from mouse ES cells (7). Spherical structures from hES cells termed embryoid bodies (EBs) resulted in the formation of beating areas and thus cardiomyocytes when differentiation was performed in serum-containing medium (7,8). Overall, these methods of differentiation rely on the presence of serum in the medium as the primary compound of the cardiomyocyte differentiation protocol and this does not lend itself to being a clinically useful and reproducible system.

It has recently been demonstrated that hES cells when co-cultured in a serum free medium in contact with a visceral endoderm-like cell line END2 resulted in the differentiation of cardiomyocytes and the appearance of beating areas (9). The majority of these hES cell-derived cardiomyocytes have a fetal ventricular-like cardiomyocyte phenotype based on their electrophysiological parameters (9). Although the bioactivity responsible for the induction of hES-derived cardiomyocytes under these co-culture conditions is under investigation it is important to note that the differentiation does not involve serum in the differentiation medium and occurs in a more defined and therefore more reproducible serum free medium (10).

Using feeder-free conditioned media (CM) allows for a more clean and controlled differentiation of cardiomyocytes than co-culturing. However, the CM from END2-cells (END2-CM) contains proteins and other molecules released from the mouse END2 cells and as such hES-derived cardiomyocytes cultured from END2-CM would be considered a "xenoproduct" for clinical purposes. Therefore, identification of the "factor(s)" produced by the END2 cell is of paramount importance to the development of a hES-derived therapeutic product.

Identifying the END2 inducing factors and other factors involved in the differentiation process has been challenging and elusive since the generation of the visceral-endoderm-like END2 cell line from a mouse P19 embryonic carcinoma cell line. Earlier data has suggested that the END2 "factor" is secreted and it is a protein. Regardless of its uncertainty on whether it is protein, it is important to identify the factor(s) if a therapeutically acceptable product is to be developed. Identifying cardiomyocyte inducing factors will provide opportunities to develop clinically-compliant populations of HES-derived cardiomyocytes.

If differentiation conditions can be established with defined culturing conditions, and without the potential presence of animal pathogens, hES-derived cardiomyocytes may be produced safely which are suitable for cardiomyocyte transplantation in patients with heart disease.

Accordingly, the invention seeks to identify factors that are involved in the process of cardiomyocyte differentiation and provide a culture system that is suitable for the induction of stem cells to cardiomyocytes and cardiac progenitors.

SUMMARY OF THE INVENTION

In a first aspect of the present invention there is provided a method of inducing or enhancing the induction of differentiation of stem cells, in particular hES cells, into embryonic germ layer derivatives such as ectoderm, mesoderm or endoderm, more preferably cardiomyocytes or cardiac mesoderm by culturing the ES cells in the presence of a defined medium that is substantially free of xeno- and serum-components and thus comprises a clinically compliant medium. The defined media comprises defined factors that contribute to the promotion of differentiation to embryonic germ layer derivatives such as ectoderm, mesoderm or endoderm, more preferably cardiomyocytes or cardiac mesoderm.

A surprisingly efficient differentiation process is now provided in which END2-CM can be replaced by a defined medium that shows equivalent cardiomyocyte inducing properties as END2-CM. One example of such fully defined medium formulation provided in this embodiment is termed defined serum free medium or bSFS. As part of the process, culture conditions are provided that are useful to maintain human embryonic stem cells in a state that promotes efficient cardiogenic differentiation.

The factors that may be present in medium contribute to the promotion of differentiation to cardiomyocytes. Preferably the factor is a prostaglandin or a p38MAP kinase inhibitor molecule. Ideally, the p38MAP kinase inhibitor molecule is a pyridinyl imidazol homologue.

A most preferred pyridinyl imidazol homologue is a small molecule, the pyridinyl imidazol homologue SB203580 or its derivatives. These may be added into media compositions such as END2-CM or bSFS which is useful to direct stem cell, in particular hES cell differentiation into germ layers such as ectoderm, mesoderm and endoderm in a concentration-dependent fashion.

In another embodiment the addition of SB203580 at higher concentrations diminishes the formation of cardiac mesoderm and subsequently cardiomyocytes and hES cell differentiation is directed toward increasing amounts of the ectodermal germ layer and in particular the neurectoderm lineage.

The factor may also be a prostaglandin such as prostaglandin I2 (PGI2), an analogue or a functional equivalent thereof. PGI2 has now been identified as an inducing factor alone or in combination with several growth factors which may act as inducing or enhancing factors to direct the differentiation of human stem cells into cardiac mesoderm and cardiomyocytes.

In a further preferred aspect the process of differentiating stem cells, in particular hES cells, into cardiomyocytes comprises growing the hES cells in the presence of a defined medium that is substantially free of xeno- and serum-components and defined factors that contribute to the promotion of differentiation to cardiomyocytes said medium further comprising at least one additive selected from the group consisting of selenium, transferrin, retinoic acid, ascorbic acid, acetic acid, hydrogen peroxide, bone morphogenetic protein and fibroblast growth factors.

In yet another aspect of the present invention there is provided a defined culture media when used for differentiating stem cells, in particular hES cells, into cardiomyocytes which is substantially free of xeno- and serum-components said defined media comprising defined factors that contribute to the promotion of differentiation to cardiomyocytes. Preferably the factor is a prostaglandin or a p38MAP kinase inhibitor molecule. Preferably, the p38MAP kinase inhibitor molecule is a pyridinyl imidazol homologue and the prostaglandin is PGI2, its analogue or a functional equivalent thereof. The defined medium may also comprise at least one additive selected from the group consisting of selenium, transferrin, retinoic acid, ascorbic acid, acetic acid, hydrogen peroxide, bone morphogenetic protein and fibroblast growth factors.

The present invention also provides cardiomyocytes and cardiac progenitors and cardiomyocyte and cardiac progenitor populations differentiated by the methods according to the present invention.

The present invention further provides a cell composition including a differentiated cell of the present invention, and a carrier.

Another aspect the invention includes a method of repairing cardiac tissue, the method including transplanting a cardiomyocyte or cardiac progenitor cell differentiated by the methods of the invention into damaged cardiac tissue of a subject.

The methods of the invention can be combined to increase observed effects in mesoderm formation and cardiac differentiation.

The invention further provides use of a cardiomyocyte of the invention in testing a drug or treatment for a cardiac condition.

BRIEF DESCRIPTION OF THE DRAWINGS

FIG. 17 shows the expression of cardiomyocyte proteins in hES-derived cardiomyocytes exposed to END2-CM. (A) Beating EBs were embedded in paraffin and serial sections prepared. Shown are immunofluorescence images of sections stained for sarcomeric Tropomyosin, MLC-2a and -2v, as well as sarcomeric myosin heavy chain (red). Nuclei are stained with DAPI (blue). (B) EBs grown for 12 days in END2-CM were digested and plated out on tissue culture trays. After growing out to a monolayer, the cells were fixed and stained for the cardiac marker Tropmyosin following the DAB protocol. (C) Instead of culture plates, digested EBs were seeded on chamberslides. Cells were fixed before reaching confluency. Immunofluorescence images of cardiomyocytes stained for α-Actinin and sarcomeric Tropomyosin.

FIG. 23 shows EBs were grown for 12 days in SF media or CM from END2 cells and treated with 10 µM SB203580; Shown are EBs attached to the surface; there is a high number of neurite-like outgrowth under serum free condition (+10 µM SB203580), typical for neural progenitor populations.

FIG. 25 shows an effect of SB203580 (SB) and acetic acid (AA) on cardiac induction when added into END2 cell conditioned media (END2-CM) or in the fully defined media bSFS; percent of beating EBs per well (shown in A), cardiac α-Myosin Heavy Chain (α-MHC) expression relative to α-Actin (shown in B), and percentage of cardiomyocytes in the cultures (shown in C) is presented. SB203580 has a strong enhancing effect on cardiomyocyte formation in different media at the 5 μM concentration tested. The cardiomyocyte inducing effect is thus not limited to END2-CM but also works efficiently in the fully defined medium bSFS. The cardiomyocyte-inducing effect is further strongly enhanced if SB203580 is added in combination with acetic acid at respective concentrations.

FIG. 28 shows (A) Prostaglandin $I_2$ (or PGI2) quantification via ELISA in END2-CM or in conditioned medium generated by the same conditioning method but utilizing the cell line MES1 that has no cardiomyocyte inductive activity. (B-C). PGI2 was added into the non-conditioned, serum free medium bSF (see example 10) at 0.2 μM or 2.0 μM concentration and hES differentiation was performed in EBs in suspension for 12 days before the percentage of beating EBs and relative expression of cardiac α-MHC expression was tested.

DETAILED DESCRIPTION OF THE INVENTION

Figure 1:
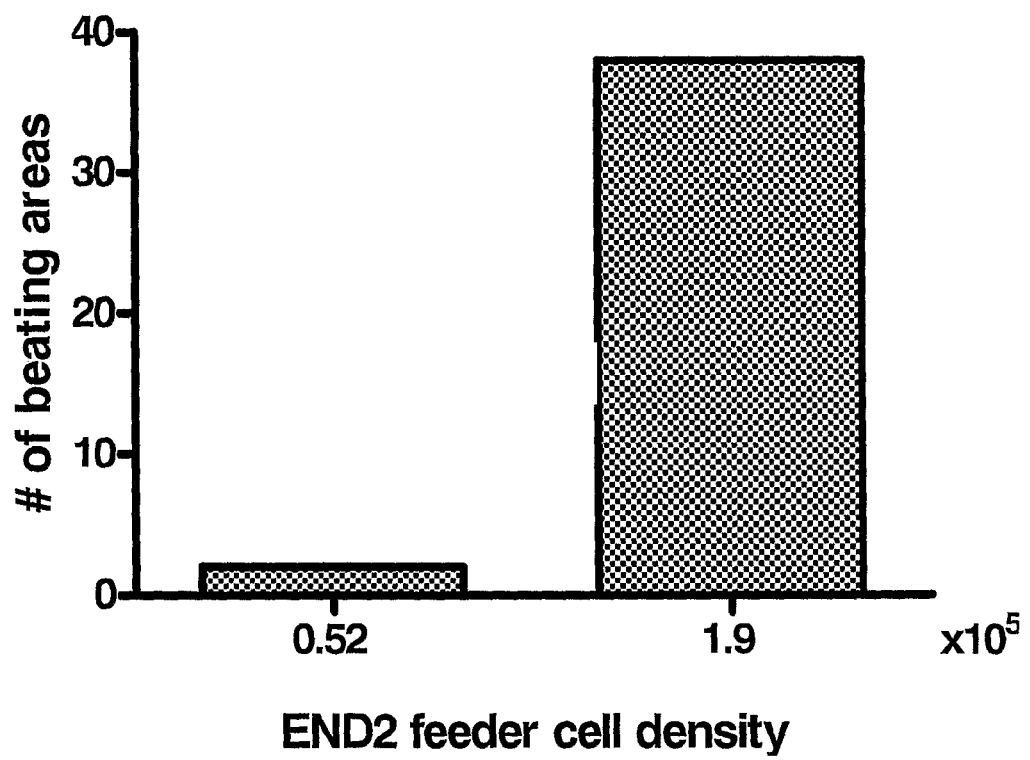
FIG. 1 shows a Histogram showing that when hES cells are co-cultured with two different END2 feeder cell densities (cells/cm$^2$) there is a marked increase in the emergence of beating areas after a period of co-culture.

In a first aspect of the present invention there is provided a method of inducing or enhancing the induction of differentiation of stem cells, in particular hES cells, into embryonic germ layer derivatives such as ectoderm, mesoderm or endoderm, more preferably cardiomyocytes or cardiac mesoderm by culturing the ES cells in the presence of a defined medium that is substantially free of xeno- and serum-components and thus comprises a clinically compliant medium. The defined media comprises defined factors that contribute to the promotion of differentiation to embryonic germ layer derivatives such as ectoderm, mesoderm or endoderm, more preferably cardiomyocytes or cardiac mesoderm.

The discovery of an inducing factor in CM is critical since the process of generating cardiomyocytes from hES cells can now be made GMP. CM from a mouse or human cell line is no longer required. It is considered to be a xeno product and very troublesome from a regulatory perspective. The present invention provides defined conditions to induce embryonic germ layer derivatives such as ectoderm, mesoderm or endoderm, more preferably cardiomyocytes or cardiac mesoderm which is both simple and cheap.

Stem Cells

In the present invention a stem cell, preferably a human stem cell is undifferentiated prior to culturing and is capable of undergoing differentiation. The stem cell may be selected from the group including, but not limited to, embryonic stem (ES) cells, pluripotent stem cells, haematopoietic stem cells, totipotent stem cells, mesenchymal stem cells, neural stem cells, or adult stem cells.

The stem cell is preferably a human embryonic stem (hES) cell which may be derived directly from an embryo or from a culture of embryonic stem cells. For example, the stem cell may be derived from a cell culture, such as human embryonic stem cells (hES) cells (Reubinoff et al., Nature Biotech. 16:399-404 2000). The stem cell may be derived from an embryonic cell line or embryonic tissue. The embryonic stem cells may be cells which have been cultured and maintained in an undifferentiated state. Such cells have been described in WO2000/027995, WO2001/042421, WO2001/098463 and WO2001/068815, the contents of which are incorporated herein by reference.

The stem cells suitable for use in the present methods may be derived from a patient's own tissue. This would enhance compatibility of differentiated tissue grafts derived from the stem cells with the patient. The stem cells may be genetically modified prior to use through introduction of genes that may control their state of differentiation prior to, during or after their exposure to the factors that contribute to the promotion of differentiation of the stem cells. They may be genetically modified through introduction of vectors expressing a selectable marker under the control of a stem cell specific promoter such as Oct-4 or of genes that may be upregulated to induce differentiation. The stem cells may be genetically modified at any stage with markers or gene so that the markers or genes are carried through to any stage of cultivation. The markers may be used to purify the differentiated or undifferentiated stem cell populations at any stage of cultivation.

It is expected that these culture conditions for improved or enhanced differentiation will be applicable at least to all stem cell lines from the same sources as those tested and suggest that these culture conditions for improved differentiation are applicable to all stem cell lines and stem cells in general. Furthermore, the fact that these differentiation conditions can be established without fetal calf serum, and thus without the potential presence of animal pathogens, increases the chance that these hES-derived embryonic germ layer derivatives such as ectoderm, mesoderm or endoderm, more preferably cardiomyocytes or cardiac mesoderm are suitable for transplantation in patients preferably with heart disease.

In a further preferred aspect the process of differentiating stem cells, in particular hES cells, into cardiomyocytes comprises growing the hES cells in the presence of a defined medium that is substantially free of xeno- and serum-components and incorporates defined factors that contribute to the promotion of differentiation to cardiomyocytes said medium further comprising at least one additive selected from the group consisting of selenium, transferrin, retinoic acid, ascorbic acid, acetic acid, hydrogen peroxide, bone morphogenetic protein and fibroblast growth factors.

Germ Layer Differentiation

The present invention relates to controlling germ layer differentiation and promoting mesoderm formation. The factors identified in the present invention have been found to be suitable for controlled differentiation of the germ layer into embryonic germ layer derivatives such as ectoderm, mesoderm or endoderm, more preferably cardiomyocytes or cardiac mesoderm. The controlled differentiation may be achieved based on the dosage of the factors. For instance, at various concentrations the factors may induce the formation of cardiac mesoderm or ectoderm, in particular, neurectoderm.

Cardiomyocyte or Cardiac Mesoderm Differentiation

The terms "cardiac differentiation", "cardiomyogenic differentiation", "cardiomyogenesis" or "differentiating stem cells into cardiomyocytes" means the formation of cardiomyocytes from stem cells preferably from hES cells. Formation of cardiomyocytes is defined by the formation of contracting EBs, contracting seeded cells, immune cytological staining for cardiomyocyte specific marker, and expression of cardiomyocyte specific marker.

Factors

The factors that may be present in medium contribute to the promotion of differentiation to cardiomyocytes. Preferably the factor is a p38MAP kinase inhibitor molecule or a prostaglandin, an analogue or a functional equivalent thereof.

(i) p38MAP Kinase Inhibitor Molecule

It has also been surprisingly found that hES cells grown on human feeders differentiate more efficiently into cardiomyocytes and additionally, the use of a small molecule that inhibits p38 MAP kinase contributes to the differentiation process.

The inhibition of p38MAPK may be by any inhibitor of the p38 MAPK pathway including inhibitors preventing the activation of MAPKAP kinase-2 and the phosphorylation of heat shock protein 27 (hsp27). At higher dosages of the inhibitor, cardiomyocyte differentiation may be inhibited and neural progenitor populations increased.

The methods of the invention involving inhibition of p38 MAPK may be carried out under serum free conditions in unconditioned media or in conditioned medium conditioned with END2 cells or cells producing the same or similar factors or bSFS.

Ideally, the p38MAP kinase inhibitor molecule is a pyridinyl imidazol homologue.

A most preferred pyridinyl imidazol homologue is a small molecule, the pyridinyl imidazol homologue SB203580 or its derivatives. These may be added into media compositions such as END2-CM or bSFS which is useful to direct stem cell, in particular hES cell differentiation into germ layers such as ectoderm, mesoderm and endoderm in a concentration-dependent fashion. In one example, addition of SB203580 is useful to efficiently induce mesoderm, especially cardiac mesoderm, and in particular cardiomyocyte differentiation from hES cells in various media compositions. Quantification of the number of cardiomyocytes either by defining percentage of beating EBs, total number of cardiomyocytes by means of immune cytochemistry, as well as cardiac marker expression (relative gene expression data using qRT-PCR) show a significant increase in cardiomyocyte formation when predetermined concentrations of SB203580 are added. The dose effect of SB203580 at lower concentrations is most prominent during early cardiac mesoderm formation and early cardiac differentiation resulting in formation of cardiomyocytes as documented in this embodiment. Thus, the surprising inductive activity of SB203580 described in this invention is entirely different to the effect of SB203580 on cell cycle re-entry of terminally differentiated, adult cardiomyocytes isolated from heart tissue observed by Engel et al, (12). Preferably the SB203580 is used in a range of approximately 0.1-100 µM, more preferably in the range of approximately 0.1-50 µM.

Applying the process in this invention it is surprisingly found that addition of Acetic Acid into bSFS alone or preferably in combination with SB203580 results in a prominent increase in cardiac differentiation.

In another embodiment the addition of SB203580 at higher concentrations diminishes the formation of cardiac mesoderm and subsequently cardiomyocytes and hES cell differentiation is directed toward increasing amounts of the ectodermal germ layer and in particular the neurectoderm lineage.

Therefore, it is preferred that to induce cardiomyocyte, SB203580 is present in the range of approximately 0.5-20 µM. Preferably, to induce neurectoderm SB203580 is present in the range of approximately 10-50 µM.

SB203580 is a specific inhibitor of the MAP kinase homologue p38 and does not inhibit the JNK and/or p42/p44 MAP kinase (13). MAP (mitogen-activated protein) kinases are a family of serine/threonine protein kinases widely conserved among eukaryotes that play a central role in integrating the signals from a diverse group of extra cellular stimuli and proto-oncogenes to the nucleus, affecting cellular processes like cell proliferation, cell differentiation, cell movement and cell death. The p38 MAP kinase is also activated in response to cellular stress. Previous published studies have shown that SB203580 prevented cardiomyocyte differentiation in the mouse embryonic carcinoma cell line P19 which can normally be induced to differentiate in vitro into either cardiomyocytes or neurons (14). More recently it has been demonstrated that inhibition of the p38 MAPK pathway impacts on the cell cycle re-entry of adult cardiomyocytes (12).

(ii) Prostaglandins

The factor may also be a prostaglandin such as prostaglandin I2 (PGI2), an analogue or a functional equivalent thereof. PGI2 has now been identified as an inducing factor alone or in combination with several growth factors which may act as inducing or enhancing factors to directly differentiate human stem cells into germ layer derivatives, in particular to cardiomyocyte induction. The prostaglandin (PGI2), its analogue or functional equivalent thereof, includes its natural breakdown form of 6-keto-Prostaglandin F1α (6k-PGF1α) and 2,3-dinor-6-keto-Prostaglandin F1α (2,3d-6k-PGF1α); its synthetic analogs, such as iloprost, cicaprost, and carbarprostacyclin (cPGI) and stable chemical structures and its derivatives. The term prostanoids also includes prostaglandins, such as prostacyclins, thromboxanes, and related substances, but "prostaglandins" is often used loosely to include all prostanoids. Accordingly the invention also includes prostanoids within its scope.

Therefore not wishing to be limited by theory, functional equivalents may also include PGA, PGB, PGC, PGD (PGD2), PGE (PGE2), PGF (PGF2a), PGI (PGI2 as exemplified), Thromboxane A2 and 12(s)-HHT. These would also include the Amide and Ester Prostanoid derivatives.

Prostaglandins have now been found to assist in the differentiation of cardiomyocytes. In particular, by adding a prostaglandin, analogue or functional equivalent thereof to a stem cell culture, cardiomyocyte differentiation may be enhanced over base line differentiation levels. For instance, where cardiomyocyte differentiation of stem cells is spontaneous or is induced under specific cardiomyocyte differentiation inducing conditions, the level of cardiomyocyte differentiation from stem cells to cardiomyocytes or cardiac progenitors can be increased resulting in increased numbers of cardiomyocytes and cardiac progenitors.

It is also conceivable for the present invention to include the use of a prostaglandin, analogue or functional equivalent thereof to induce germ layer derivatives, in particular cardiomyocyte differentiation from an undifferentiated hES cell population that is capable of differentiation to germ layer derivatives, especially cardiomyocytes and cardiac progenitors and preferably to direct and induce the differentiation toward a cardiomyocyte lineage.

The addition of a prostaglandin, analogue or functional equivalent thereof is applicable to any method that is directed to differentiation of stem cells to germ layer derivatives, especially cardiomyocytes and cardiac progenitors including both directed and spontaneous differentiation.

The prostaglandin, analogue or functional equivalent thereof may be introduced at any stage of the culture. Preferably the prostaglandin, analogue or functional equivalent thereof may be present continuously from the initial stage of culture of a stem cell or preferably of a co-culture of the stem cells.

(iii) Prostaglandin I2 (PGI2)

Prostaglandin I2 (prostacyclin) has now been identified as a preferred inducing factor alone or in combination with several growth factors which may act as inducing or enhancing factors to direct and induce differentiation of human stem cells into germ layer derivatives, especially cardiomyocytes and cardiac progenitors. The discovery of PGI2 as the inducing factor in CM is a critical one since the process of generating cardiomyocytes from hES cells can be made GMP. CM from a mouse cell line is no longer necessary, which is considered to be a xeno product and troublesome from a regulatory perspective.

Prostacyclin is an unstable prostaglandin released by mast cells and endothelium and is mainly synthesized by vascular endothelium and smooth muscle. It is a potent inhibitor of platelet aggregation and also causes vasodilation and increased vascular permeability. Release of PGI2 is enhanced by bradykinin. However, this compound has not been previously associated with the process of cardiomyocyte differentiation nor the induction of that process.

Whilst PGI2 has been found to be an inducing factor for cardiomyocyte differentiation, analogues of PGI2 such as but not limited to Beraprost, clinprost and PGI1-Na are also included in the present invention. Any one of the analogues that are commonly available is within the scope of the present invention. Preferably the analogue is a stable analogue that is capable of prolonged culture. It must be suitable for inclusion into media for the cardiomyocyte induction.

The term "functional equivalent" also includes those compounds that can behave in the same manner and essentially act like PGI2.

The present invention also includes the addition of components that form PGI2. For instance, PGI2 is derived from arachidonic acid and produced by the cyclooxygenase (COX) system. Arachidonic acid, is first converted to PGH2 by prostaglandin-endoperoxide synthase (Ptgs or Cox), and PGH2 is subsequently converted to PGI2 by the action of prostacyclin synthase (Ptgis). Therefore any of the compounds that contribute to the generation of PGI2 in culture are also included in the scope of the present invention.

The present invention provides a method to improve current culturing methods for the differentiation of embryonic germ layer derivatives such as ectoderm, mesoderm or endoderm, more preferably cardiomyocytes or cardiac mesoderm by improving induction of differentiation. Hence this can include increasing the number of embryonic germ layer derivatives such as ectoderm, mesoderm or endoderm, more preferably cardiomyocytes or cardiac mesoderm differentiated in a culture compared with a culture that is not enhanced and improving the efficiency of the embryonic germ layer derivatives such as ectoderm, mesoderm or endoderm, more preferably cardiomyocytes or cardiac mesoderm differentiation process. This can also include inducing the embryonic germ layer derivatives such as ectoderm, mesoderm or endoderm, more preferably cardiomyocytes or cardiac mesoderm from an undifferentiated stem cell culture that is capable of embryonic germ layer derivatives such as ectoderm, mesoderm or endoderm, more preferably cardiomyocytes or cardiac mesoderm differentiation.

Whilst the invention seeks to provide a culture system absent of xenoproducts, a co-culture system may be improved by improving the co-cultured cells as providing inducers of embryonic germ layer derivatives such as ectoderm, mesoderm or endoderm, more preferably cardiomyocytes or cardiac mesoderm differentiation. Accordingly, methods to enhance PGI2 release from the cells are within the scope of the present invention. Hence, co-cultured cells such as endothelial cells may be modified to induce the release of inducers such as PGI2, preferably by the use of compounds such as bradykinin.

Similarly, co-cultured cells may be genetically modified to increase PGI2 release wherein activating enzymes such as prostaglandin endoperoxidase synthase (Ptgs or Cox) and prostacyclin synthase (Ptgis) in the presence of arachidonic acid are further up-regulated to increase PGI2 release.

The concentration of PGI2, an analogue or functional equivalent thereof may be present in a range of 2 nM to 200,000 nM. Preferably the PGI2 is present in the range of 200 nM to 20,000 nM. More preferably, PGI2 is present in the range of 200 nM to 2,000 nM. However, these amounts closely approximate the effect on induction of cardiomyocyte differentiation that conditioned media has on the cells. Most preferably, the concentration of the pGI2 in the media is 20 nM.

Culture Media and Factors

In yet another aspect of the present invention there is provided a defined culture media when used for differentiating stem cells, in particular hES cells, into embryonic germ layer derivatives such as ectoderm, mesoderm or endoderm, more preferably cardiomyocytes or cardiac mesoderm which is substantially free of xeno- and serum-components said defined media comprising defined factors that contribute to the promotion of differentiation to embryonic germ layer derivatives such as ectoderm, mesoderm or endoderm, more preferably cardiomyocytes or cardiac mesoderm. Preferably the factor is a prostaglandin its analogue or functional equivalent thereof or a p38MAP kinase inhibitor molecule.

Preferably, the p38MAP kinase inhibitor molecule is a pyridinyl imidazol homologue and the prostaglandin is PGI2, an analogue or a functional equivalent thereof. The defined medium may also comprise at least one additive selected from the group consisting of selenium, transferrin, retinoic acid, ascorbic acid, acetic acid, hydrogen peroxide, bone morphogenetic protein and fibroblast growth factors.

Preferably the culture media is capable of delivering a final concentration of the prostacyclin (PGI2), an analogue or functional equivalent thereof to a culture of stem cells in the range of 2 nM to 20000 nM. More preferably the final concentration is in the range of 200 nM to 2000 nM. A person skilled in the art will appreciate that a suitable concentration can be determined by suitable trial and experimentation given the above amounts.

The culture media may be any media that supports stem cell differentiation. Preferably, the media is a DMEM based media and it may be supplemented with growth factors and essential minerals including β-ME, non-essential amino acids, and L-glutamine. However, it is preferred to induce cardiomyocyte differentiation in a serum-free media. It is also preferred that insulin is not present in the media or is at least reduced, preferably to below 10 ng/ml and is most preferably absent.

The invention also provides use of serum free medium containing a prostaglandin, analogue or functional equivalent thereof for use in a method of inducing differentiation of stem cells into cardiomyocytes and cardiac progenitors.

Germ Layer Derivative Cell Compositions

The present invention also provides embryonic germ layer derivatives such as ectoderm, mesoderm or endoderm, more preferably cardiomyocytes or cardiac mesoderm, cardiac progenitors prepared by the methods according to the present invention.

The cardiomyocytes, cardiac mesoderm and cardiac progenitors of the invention are preferably capable of beating. Cardiomyocytes and the cardiac progenitors can be fixed and stained with α-actinin antibodies to confirm muscle phenotype. α-troponin, α-tropomyosin and α-MHC antibodies also give characteristic muscle staining.

The present invention also provides a mutated differentiated embryonic germ layer derivatives such as ectoderm, mesoderm or endoderm, more preferably cardiomyocytes, cardiac mesoderm or cardiac progenitor of the invention prepared from a mutant stem cell. It will be recognized that methods for introducing mutations into cells are well known in the art. Mutations encompassed are not only mutations resulting in the loss of a gene or protein but also those causing over expression of a gene or protein.

The present invention further provides a cell composition including a differentiated cell of the present invention, and a carrier. The carrier may be any physiologically acceptable carrier that maintains the cells. It may be PBS or other minimum essential medium known to those skilled in the field. The cell composition of the present invention can be used for biological analysis or medical purposes, such as transplantation.

In another aspect there is provided a cell population comprising a greater proportion of an embryonic germ layer derivative that has selectively differentiated in a defined medium that is substantially free of xeno- and serum-components said defined medium comprising defined factors that selectively promote the differentiation of stem cells to the embryonic germ layer derivative.

The germ layer derivative cell compositions or populations may comprise a higher percentage of a cell type or lineage compared to cell populations that have derived spontaneously. This is due to the induced and directed differentiation toward certain cell types of the embryonic germ layer derivatives such as ectoderm, mesoderm or endoderm, more preferably cardiomyocytes or cardiac mesoderm described in the present invention by the use of inducing factors that favour or select for differentiation of the stem cell to a particular embryonic germ layer derivative.

The cell compositions of the present invention can be used in methods of repairing or treating diseases or conditions, such as cardiac disease or where tissue damage has occurred. The treatment may include, but is not limited to, the administration of cells or cell compositions (either as partly or fully differentiated) into patients. These cells or cell compositions would result in reversal of the condition via the restoration of function as previously disclosed above through the use of animal models.

Methods of Use

The present invention also provides differentiated cells produced using methods of the invention that may be used for transplantation, cell therapy or gene therapy. Preferably, the invention provides a differentiated cell produced using methods of the invention that may be used for therapeutic purposes, such as in methods of restoring cardiac function in a subject suffering from a heart disease or condition or restoring neural function in a subject suffering from a neurological condition.

Another aspect of the invention is a method of treating or preventing a cardiac disease or condition or a neurological condition. Cardiac disease is typically associated with decreased cardiac function and includes conditions such as, but not limited to, myocardial infarction, cardiac hypertrophy and cardiac arrhythmia. In this aspect of the invention, the method includes introducing an isolated differentiated cardiomyocyte cell of the invention and/or a cell capable of differentiating into a cardiomyocyte cell when treated using a method of the invention into cardiac tissue of a subject. The isolated cardiomyocyte cell is preferably transplanted into damaged cardiac tissue of a subject. More preferably, the method results in the restoration of cardiac function in a subject.

In yet another aspect of the invention there is provided a method of repairing cardiac tissue, the method including introducing an isolated cardiomyocyte or cardiac progenitor cell of the invention and/or a cell capable of differentiating into a cardiomyocyte cell when treated using a method of the invention into damaged cardiac tissue of a subject.

It is preferred that the subject is suffering from a cardiac disease or condition. In the method of repairing cardiac tissue of the present invention, the isolated cardiomyocyte cell is preferably transplanted into damaged cardiac tissue of a subject. More preferably, the method results in the restoration of cardiac function in a subject.

The present invention preferably also provides a myocardial model for testing the ability of stem cells that have differentiated into cardiomyocytes to restore cardiac function.

The present invention preferably provides a myocardial model for testing the ability of stem cells that have differentiated into cardiomyocytes or cardiac progenitors using methods of the invention to restore cardiac function. In order to test the effectiveness of cardiomyocyte transplantation in vivo, it is important to have a reproducible animal model with a measurable parameter of cardiac function. The parameters used should clearly distinguish control and experimental animals [see for example in Palmen et al. (2001), Cardiovasc. Res. 50, 516-524] so that the effects of transplantation can be adequately determined. PV relationships are a measure of the pumping capacity of the heart and may be used as a read-out of altered cardiac function following transplantation.

A host animal, such as, but not limited to, an immuno-deficient mouse may be used as a 'universal acceptor' of cardiomyocytes from various sources. The cardiomyocytes are produced by methods of the present invention.

The myocardial model of the present invention is preferably designed to assess the extent of cardiac repair following transplant of cardiomyocytes or suitable progenitors into a suitable host animal. More preferably, the host animal is an immunodeficient animal created as a model of cardiac muscle degeneration following infarct that is used as a universal acceptor of the differentiated cardiomyocytes. This animal can be any species including but not limited to murine, ovine, bovine, canine, porcine and any non-human primates. Parameters used to measure cardiac repair in these animals may include, but are not limited to, electrophysiological characteristic of heart tissue or various heart function. For instance, contractile function may be assessed in terms of volume and pressure changes in a heart. Preferably, ventricular contractile function is assessed. Methods of assessing heart function and cardiac tissue characteristics would involve techniques also known to those skilled in the field.

The present invention also provides a model for the study of human cardiomyocytes in culture, comprising differentiated cardiomyocytes or cardiac progenitors of the invention. This model is useful in the development of cardiomyocyte transplantation therapies.

Further, the present invention provides an in vitro system for testing cardiovascular drugs comprising a differentiated cardiomyocyte of the invention.

Throughout the description and claims of this specification, the word "comprise" and variations of the word, such as "comprising" and "comprises", is not intended to exclude other additives, components, integers or steps.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed in Australia before the priority date of each claim of this application.

The present invention will now be more fully described with reference to the accompanying examples and drawings. It should be understood, however that the description following is illustrative only and should not be taken in any way as a restriction on the generality of the invention described above.

EXAMPLES

Example 1

Development and Optimization of Serum Free END2 Conditioned Media

1. Material and Methods (i) hES cells: The hES cell lines hES2, hES3, hES3-GFP (16) and hES4 from ES Cell International (http://stemcell-s.nih.gov/research/registry/esci.asp) at passage numbers ranging between 75-125 with a normal karyotype were used.

(ii) END2 cells: END2 cells are a visceral-endoderm-like cell line derived from P19 cells, a mouse embryonal carcinoma cell line (10). END2 cells were cultured as described previously (17).

(iii) Culture Media:

hES medium: For maintaining hES cells on mouse embryonic feeder cells (MEF), hES were grown in DMEM supplemented with 20% FCS, 0.1 mM β-mercaptoethanol, 1×MEM non-essential amino acids, 2 mM L-glutamine and antibiotics (Penicillin/Streptomycin). hES cells cultured on HF were grown in KO-DMEM with 20% KOSR in 0.1 mM β-mercaptoethanol, 1% MEM non-essential amino acids, 2 mM L-glutamine, bFGF (10 ng/ml) with or without antibiotics (Penicillin/Streptomycin; all reagents from Invitrogen).

SF medium: DMEM supplemented with MEM 1× non-essential amino acids, 2 mM L-Glutamine, 1× Insulin-Transferrin-Selenium, 0.1 mM β-mercaptoethanol with or without Penicillin/Streptomycin (all reagents from Invitrogen). The medium was used to generate END2-CM or directly for hES differentiation.

END2-CM: To generate END2-CM SF medium was added to END2 cell cultures as described below.

(iv) Culture of hES Cells on Feeder Cells:

hES cells were grown on mouse embryonic feeder cells as published previously (2,16). In short, hES cells were cultured on Mitomycin C (10 µg/ml, Sigma) treated mouse embryonic feeder cells (MEF) in hES medium and passaged every 7 days. For passaging hES cells were either pre-treated with collagenase IV (Gibco) for 3 min followed by mechanical dissociation or without collagenase and collected after mechanical dissociation only. Harvested cells were then transferred to newly prepared feeder cells and split 1-in-4 up to 1-in-6, respectively. Enzymatically passaged cells were discarded after 20 passages and cells maintained by mechanical passaging only were newly adapted to the collagenase IV passaging method.

(v) Preparation of END2 Conditioned Medium:

This procedure describes the preparation of END2 cell conditioned medium (END2-CM).

For the production of END2-CM END2 cells were seeded at a density of $1.4 \times 10^5$ cells/$cm^2$ in a T175 flask (Nunc) and were grown for about 3 days in Dulbecco's Modified Eagle's Medium (DMEM)/F12 media (Invitrogen) supplemented with 7.5% fetal calf serum (FCS; Hyclone) until confluency. The confluent END2 cell layer was washed once in $PBS^+$ (Gibco) and serum free DMEM medium (around 200 µl of serum free DMEM per $cm^2$ of END2 growth area) was added to start the conditioning process.

The conditioning period ranged from 4 to 7 days. For harvest the medium was removed from the tissue culture flask and filtered with a disposable filtration system (0.22 µM, Millipore). The filtered END2-CM can be used immediately or stored at 4° C. or at −80° C. END2-CM can be prepared from END2 cells with passage numbers higher than 45 without loss of its cardiomyocyte inducing activity.

(vi) hES Differentiation in Suspension Culture:

This method describes hES differentiation through the formation of embryoid bodies (EB) from hES cells grown on MEF. EBs can also be generated from hES grown in feeder free systems. Formed EBs were then cultured in respective media such as SF or END2-CM. Contracting EBs resulting from cardiomyocyte differentiation were usually observed about 9 days after EB formation. Qualitative and quantitative assessment of beating EBs, determination of the relative and absolute number of formed cardiomyocytes, collection of RNA for quantitative RT-PCR, and other assays were usually performed 12-13 days after EB formation.

Enzymatically passaged hES cells grown on feeder cells were washed once with $PBS^+$ and treated with Collagenase IV (1 mg/ml) for 3-4 min at 37° C. The Collagenase IV solution was replaced by DMEM and the cells were mechanically dissociated with a pipette tip. Cells were then harvested using a cell scraper and the cell suspension was transferred to a 50 ml tube (Falcon). Cell clumps were collected by gravity and the supernatant was aspirated. Cells were resuspended in fresh DMEM medium aiming to uniformly disperse the cell clumps in the suspension. An equal volume of the cell suspension was then transferred to ultra low attachment plates (Costar). Usually 6-well plates were used and cells were cultured in 2 ml of medium. Alternatively, cells can be seeded into plates under conditions supporting cell adherence to induce differentiation of hES attached to a surface.

In suspension culture, EBs were formed in ultra low attachment plates in SF medium over night. After over night incubation SF medium was replace by fresh SF medium or END2-CM respectively for further differentiation. Subsequent medium changes were performed every 3-4 days. Usually, cells were cultured over a period of 12-13 days before the visual analysis of the proportion of beating EBs under a microscope was performed followed by cell collection for additional readouts. Multiple beating areas on single EBs were not counted separately. Values are expressed as a percentage of contracting EBs compared to non-contracting EBs in a single well of a 6-well tray. Cell harvest and analysis at time points other then 12-13 days after EB formation is indicated in the respective examples and figures of this embodiment. For EB scoring and other analytical methods hES differentiated was performed in triplicates applying the same culture conditions (e.g. the same medium added) in 3 independent wells of a 6-well plate. An average value per well was calculated and presented.

Alternatively, EBs can also be formed by culturing hES directly END2-CM or other suitable media without prior incubation in SF media over night. Different types of culture vessels that support cell cultivation in suspension culture such as Petri dishes, spinner flasks or other types of bioreactors might be used (18).

(viii) RT-PCR for Cardiac Markers:

RNA extraction: EBs at the end of the twelve day period or as indicated in the text were harvested. All EBs from 3 wells were pooled and washed once in PBS$^-$. Trizol (Invitrogen) was added before freezing the EBs at −80° C. to enhance cell lysis. Frozen samples were thawed and harshly mixed. Chloroform was added to the sample and incubated for 3 min at room temperature. The sample was centrifuged for 15 min at 13000 rpm at 4° C. and the aqueous phase collected. An equal volume of 70% ethanol was added before the sample was loaded onto an RNeasy mini column (Qiagen). The column was centrifuged for 15 sec at ≥8000 g. The rest of the purification steps were performed according to manufacturer's instructions. RNA was eluted in RNase-free water. 5 µg of the RNA sample were then treated with DNase (Invitrogen) in a volume of 50 µl. The mixture was incubated at room temperature for 30 min and heat inactivated for 10 min at 80° C. before cooling rapidly on ice.

Reverse transcriptase: 5 µg of total RNA was mixed with 2 µl of 3 µg/µl random primers (Invitrogen) in a final volume of 100 µl. 75 µl were reversed transcribed (BioLabs), the remaining 25 µl served as a negative control. Samples were incubated for 1 hour at 37° C. before the reaction was terminated for 5 min at 95° C.

Real-time PCR: The PCR reaction was performed on 100 ng of cDNA, with 15 µl of 2× IQ™ SYBR® Green Supermix (Biorad) in a final reaction volume of 30 µl. To minimize variations in the triplicates, a master mix was prepared containing all reaction components except cDNA. PCR was performed on an iCycler™ (Biorad), annealing at 58° C. for 30 sec, extension at 72° C. for 45 sec, 40 cycles in total. Relative expression values were obtained by normalizing $C_T$ values of the tested genes in comparison with $C_T$ values of the housekeeping gene α-Actin using the $\Delta\Delta C_T$ method (19). The samples were subjected to PCR amplification with human gene primers including:

α-MHC (sense primer: ATTGCTGAAACCGA-GAATGG; antisense primer: CGCTCCTTGAGGTT-GAAAAG) and NKX2.5 (sense primer: AGAAGACAGAGGCGGA-CAAC; antisense primer: CGCCGCTCCAGTTCATAG). The results were normalized to Actin (sense primer: CAATGTGGCCGAGGACTTTG; antisense primer: CATTCTCCTTAGAGAGAAGTGG). All reactions were run in triplicate.

(ix) Statistical analysis: All data are presented as mean±SEM using the statistical software provided by GraphPad Prism®, version 4.01.

2. Results

Initial co-culture experiments: Cardiomyocyte differentiation of hES cells has been performed originally by removing the hES cells from MEFs and culturing the hES cell clumps on Mitomycin C (MitC) inactivated mouse P19 derived END2 cells in DMEM medium containing 20% FBS (10,17). Beating areas emerged around 9-10 days after initiating the co-culture and follow up experiments revealed that the yield of beating areas can be increased by removing serum from the culture medium (9).

It was observed very early in the co-culture experiments that END2 cells had to be plated at a certain seeding density to induce cardiomyocyte differentiation in hES cells. END2 cells were initially plated out at a cell density of $1.9\times10^5$ cells/well (12 well plates) or $0.5\times10^5$ cells/cm$^2$ as specified by protocols obtained from Christine Mummery (personal communication). Only a very low number of beating areas were observed at day 12.

Therefore the seeding density of the END2 cells was increased four fold to ~$1.9\times10^5$ cells/cm$^2$ or $7.0\times10^5$ cells/well (using 12 well plates). This resulted in a marked increase in the emergence of beating areas being induced (FIG. 1). and was a first indication that the cardiomyocyte inducing activity coming from the END2 cell layer may be cell number and therefore possibly concentration dependent in its activity.

Figure 2:
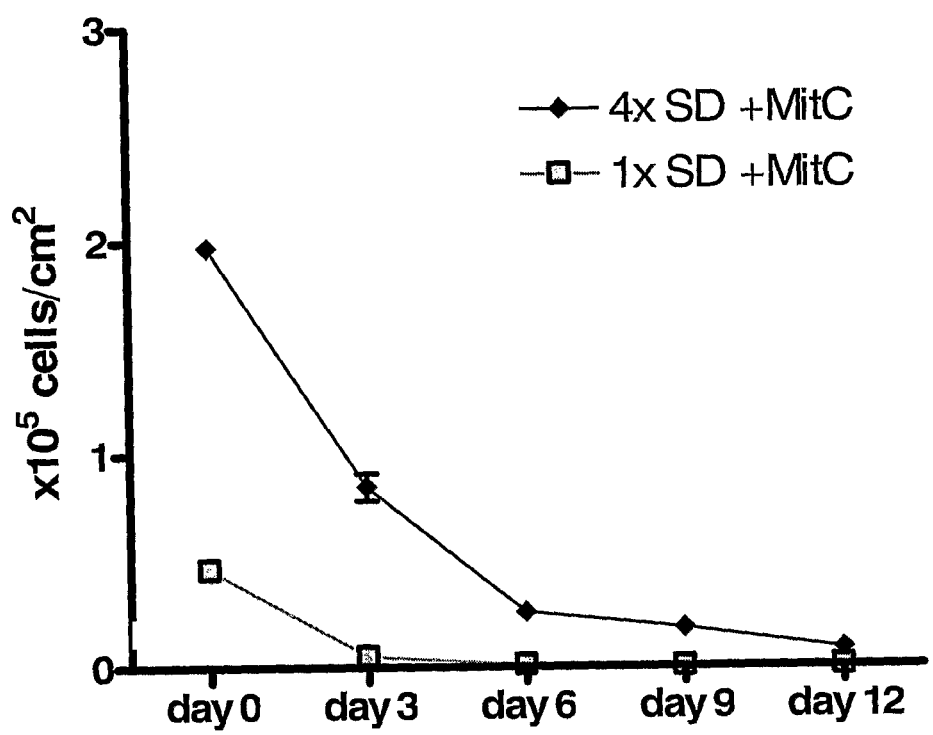
FIG. 2 shows a decrease in cell viability of MitC treated END2 cells seeded at two different densities (1× and 4×) in serum free DMEM.

To determine the number of END2 cells present over the 12 day period of co-culture END2 cell numbers were counted over a period of time in serum free culture without hES cells being seeded onto them. Two different seeding densities of Mit C treated END2 cells were plated out on to 12 well plates. The viable END2 cell number was followed over the time period equivalent to the 12 day co-culture period and at the respective days a cell count for viable END2 cells was performed (FIG. 2). Cells were plated out at either 1× seeding density ($1.9\times10^5$ cells/well) or a 4× seeding density ($7.0\times10^5$ cells/well) following the same protocol used when seeding END2 for a co-culture experiment. The viable END2 cell number under both conditions dropped rapidly in the first 6 days and there are almost no viable END2 cells left during the second period of the experiment.

Figure 3A:
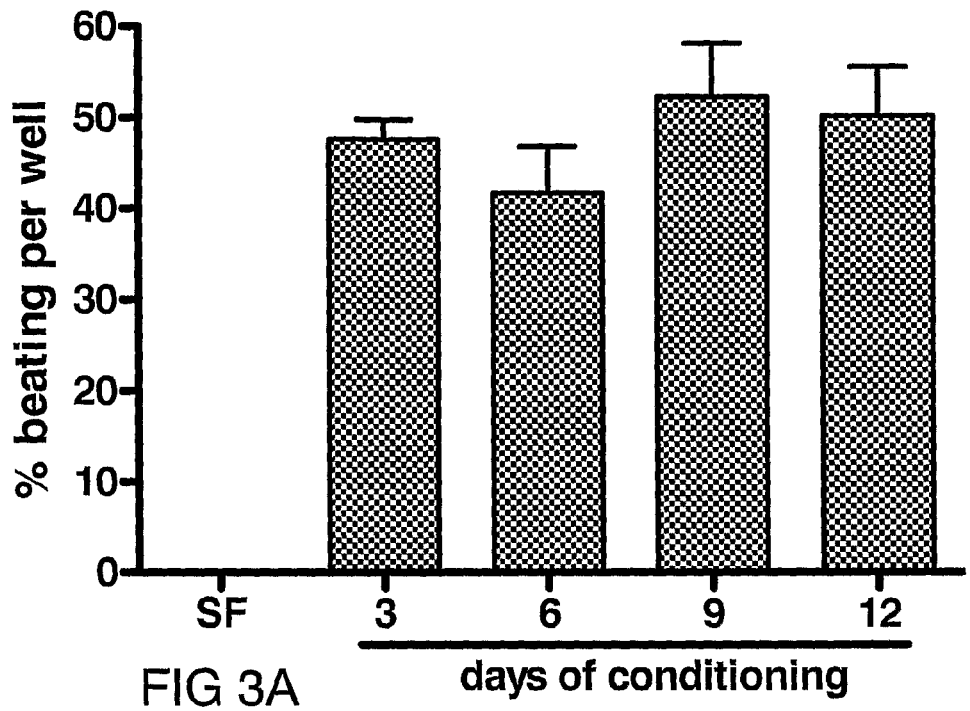
FIG. 3 shows a determination of minimal exposure time to END2-CM sufficient to effect cardiomyogenesis. EBs were cultured in CM for either 3, 6, 9 or 12 days before the medium was changed to SF media for the rest of the differentiation process. Scoring was performed at day 12 and EBs were collected for RNA extraction followed by RT-PCR.
Figure 3B:
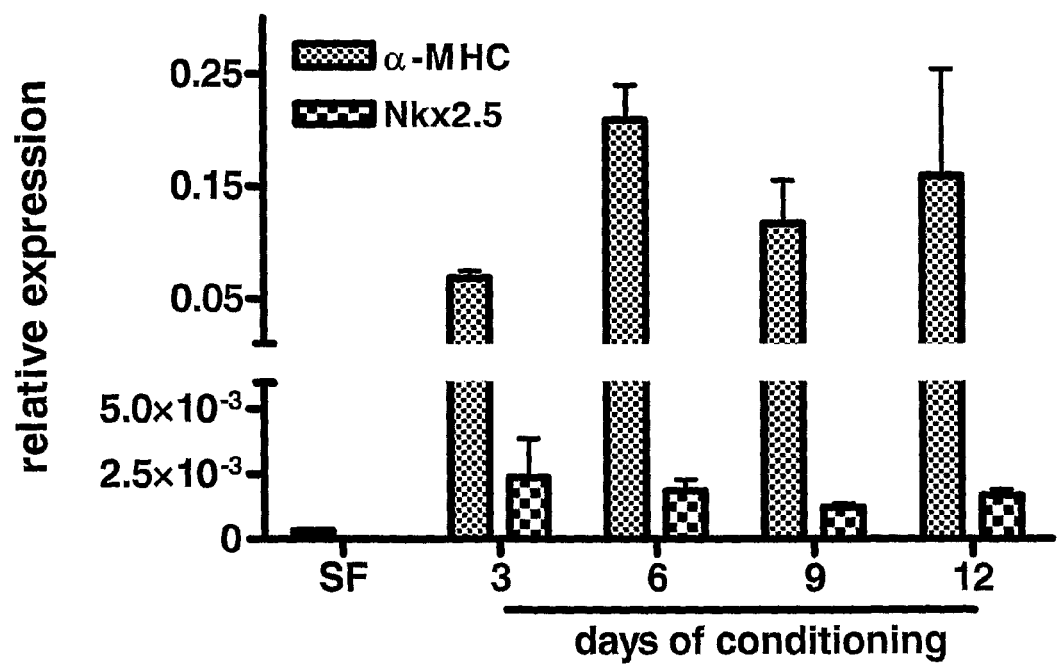

It was concluded from this experiment that whatever factor is released from END2 cells is likely to only be critical for initiating cardiomyocyte differentiation during the first 4-6 days of the experiment. Further experiments using a suspension culture system confirmed that growing EBs the first 3-6 in END2-CM is sufficient to induce cardiac differentiation (see below, FIG. 3). This is also in good agreement with data from Passier et al suggesting that the first 6 days of co-culture in serum free media was the period when cardiogenesis was occurring (9).

Figure 4:
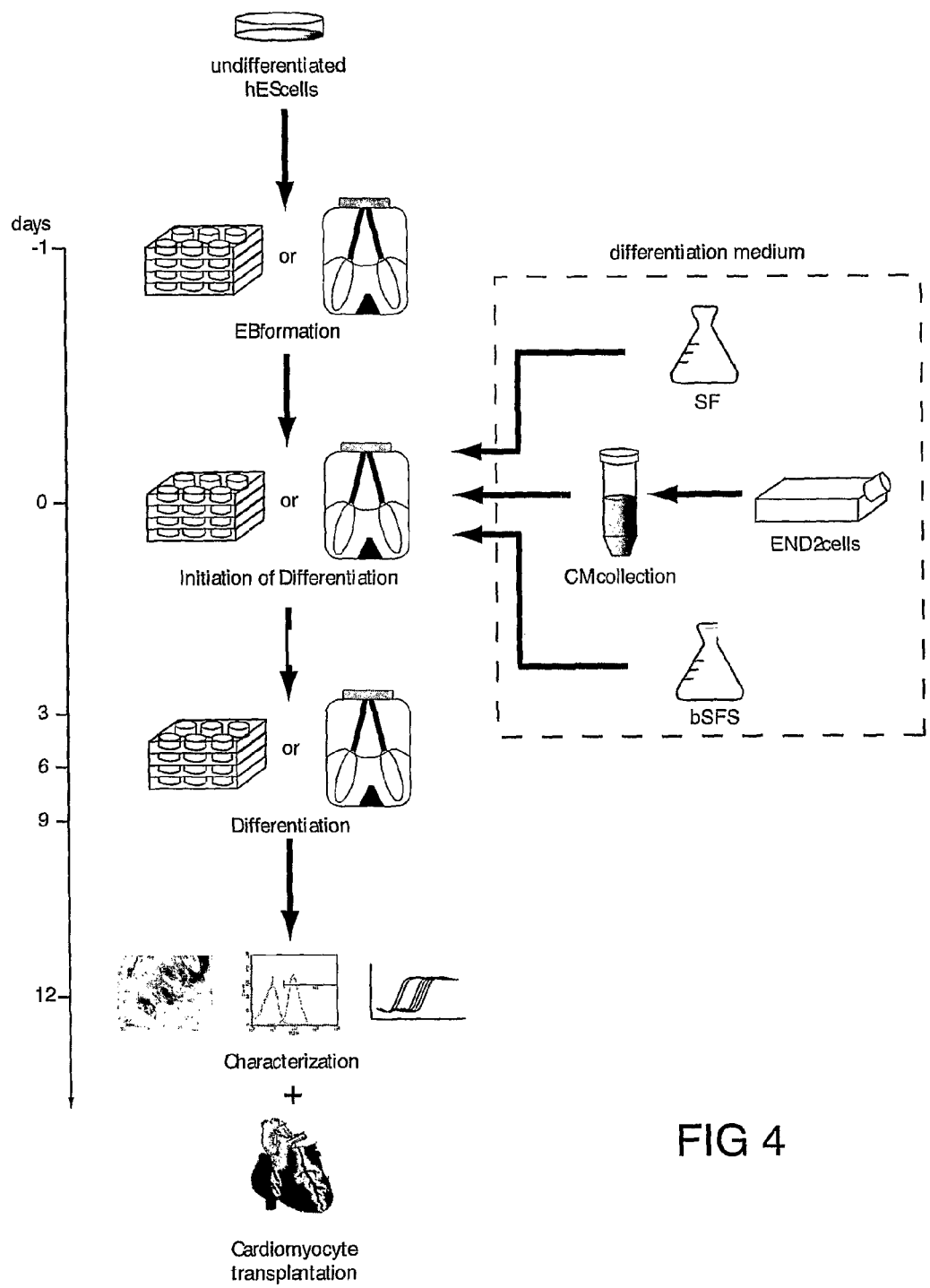
FIG. 4 shows a flowchart outlining the bioprocess utilized for the generation of cardiomyocytes in suspension culture. Enzymatic-passaged hES cells were used to form EBs overnight in SF. EBs were then grown in one of the three differentiation media (SF, END2-CM or bSFS (see Example 8) for 12 days before scored for beating areas.
Figure 5:
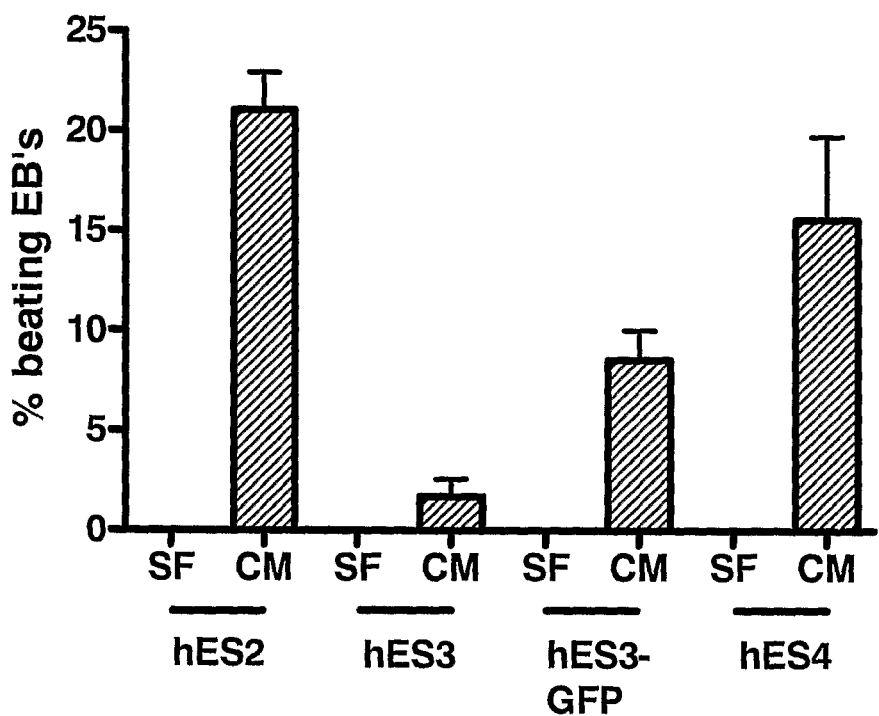
FIG. 5 shows a response of three hES cell lines to treatment with END2-CM. EBs were formed over night in SF medium followed by 12 days in SF or CM. Medium was changed every 3 days. EBs were scored for beating foci at day 12. Data are combined from individual experiments.

From adherent hES culture to suspension culture: The protocol was adapted further by forming EBs from hESC and growing them in suspension utilizing END2-CM. In short, by using Collagenase IV hESC colonies were dissociated to small cell clumps. These clumps formed embryoid bodies (EBs) over night in SF medium before being transferred to END2-CM. The cells differentiate over the following 12 days with regular medium changes every 3 days. During EB formation and differentiation, the cultures are kept in a suspension on low attachment plates and the EBs are scored for the appearance of beating foci at day 12 (FIG. 4). A cell concentration of around $8\times10^5$ hES cells/ml is seeded during experimental set-up. Not all cell clumps form EBs over night and smaller cell aggregates are removed during the first media change. Generally around $1.8 \times 10^6$ cells/ml are obtained after 12 days of differentiation in END2-CM. EBs growing in either condition, SF or END2-CM, are starting to become cystic around day 6. Beating foci normally evolve near cystic areas in EBs growing under END2-CM. Beating emerging under SF conditions over a large number of experimental set-ups supporting the specificity of END2-CM in inducing cardiomyogenesis in differentiating hESC was not observed. A high percentage of contracting EBs utilizing this protocol when using hES2, hES3 and hES4 cells (FIG. 5) was successfully generated. EBs and cardiomyocytes from hESC derived from feeder free culture system (FIG. 6) could also be formed.

Optimization of END2-CM: For the production of END2 conditioned medium the cells were seeded at a density of $1.4 \times 10^5$ cells/cm$^2$, the same seeding density used for maintaining END2 cells in culture, and the END2 cells were grown over 3 days to confluency in serum containing medium thereby reaching a cell number of around $2.4 \times 10^5$ cells/cm$^2$ in a T175 flask. The confluent END2 cell layer was then washed in PBS and SF medium was added to start the conditioning process.

Figure 7:
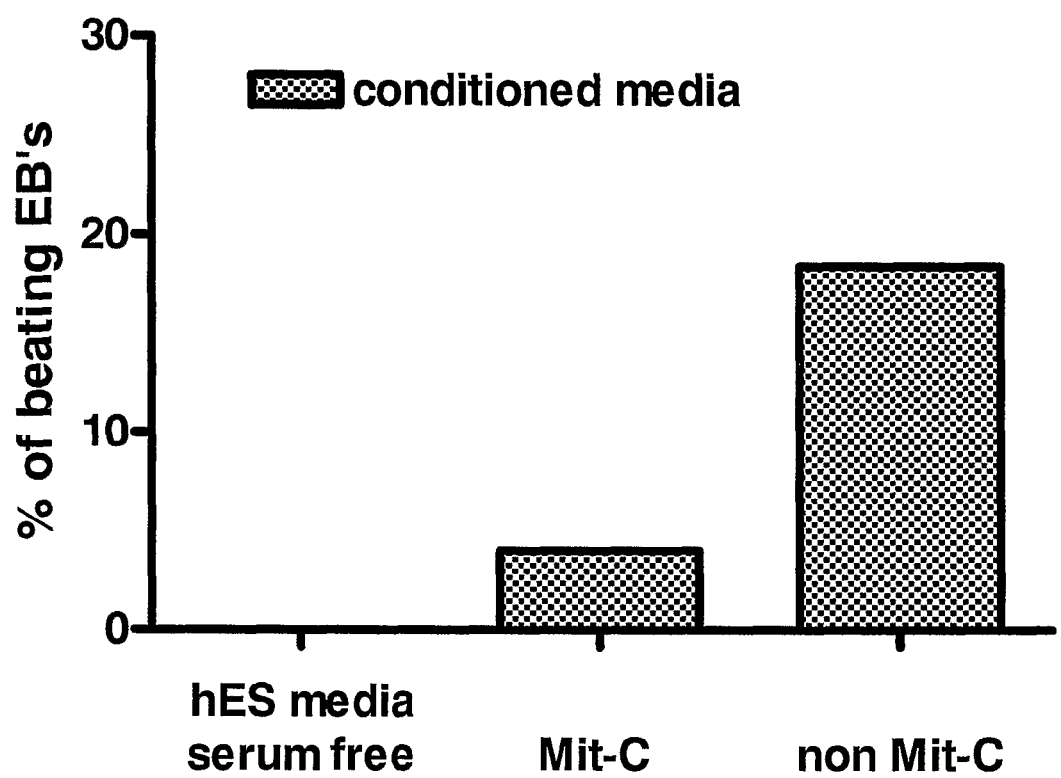
FIG. 7 shows the effect of generating END2-CM on mitotically active or inactive END2 cells. Percentage of beating EBs obtained after being cultured in day 7 CM from END2 cells either treated with MitC or untreated before the seven day conditioning period. Serum free unconditioned media served as a negative control. No beating EBs are observed.

In FIG. 7 conditioned medium from END2 cells grown to confluency in serum containing medium was compared against END2 cells that have also been grown to confluency but which have been treated with MitC before the conditioning period started.

It is noteworthy that conditioned medium from MitC treated END2 cells was far less efficient at inducing beating EBs than CM from END2 that were untreated. There was also a high percentage of cell death occurring for EBs cultured in END2-CM from MitC treated END2 cells.

Minimum period of conditioning: On the basis of data from Passier et al the first 6 days of co-culture in serum free conditions is important for specification of the cardiomyocyte lineage (9). The initial period of media conditioning was done over 7 days. This time period was later reduced to 4 days without observing an apparent decrease in cardiomyocyte induction at least as assessed by the ability to induce the formation of beating embryoid bodies (Table 1). Currently, four days is used for standard preparation of END2 conditioned medium.

TABLE 1

Conditioning period of END2 cell line and the appearance of cardiomyocyte inducing activity

| | Day 1 | Day 2 | Day 3 | Day 4 | Day 5 | Day 6 | Day 7 |
|---|---|---|---|---|---|---|---|
| Activity | − | − | − | + | + | + | + |

Filtered media was collected and used to grow newly formed EBs from hES cultures over a period of 12 days (FIG. 4). Conditioning of the END2 cells over a longer period of 7 days does not lead to an increase in the number of beating areas counted at day 12. However, END2-CM cultured on END2 cells for less than 4 days decreased the number of beating areas significantly (data not shown).

Figure 8:
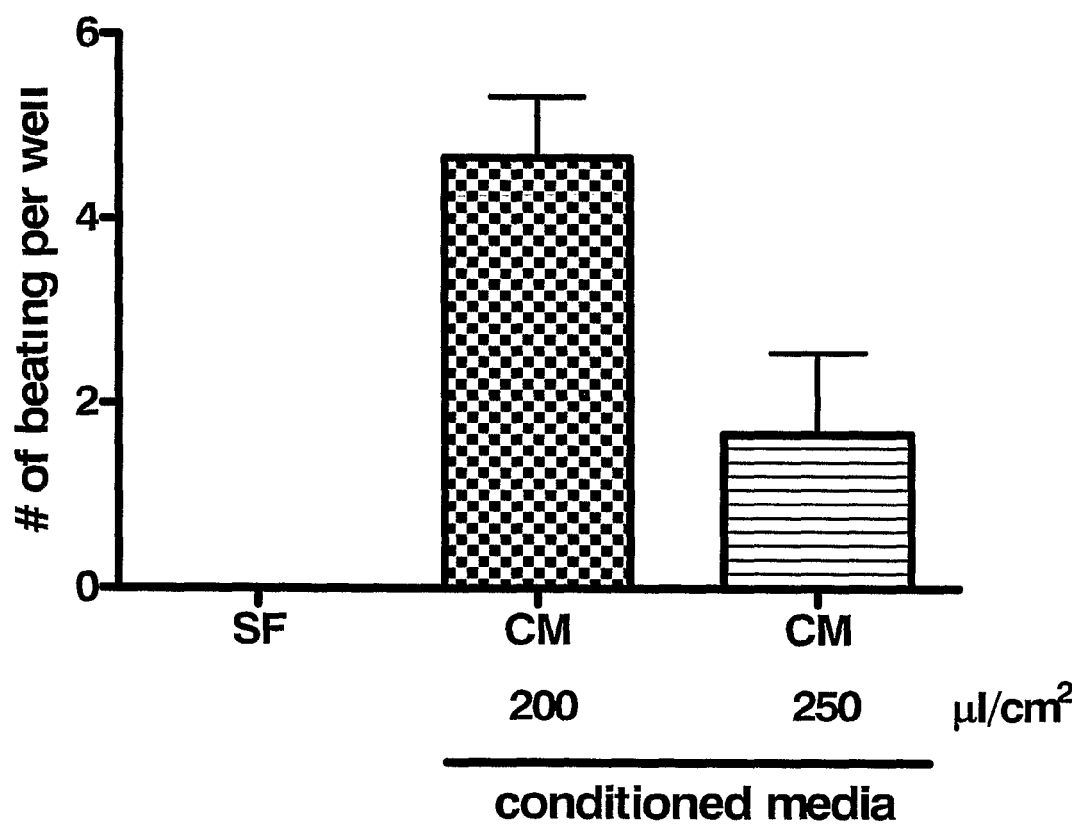
FIG. 8 shows the effect of media volume used for conditioning on END2 cells. EBs were grown for 12 days in serum-free media or CM from END2 cells. The CM was either prepared with 200 μl/cm$^2$ serum-free hES medium or 250 μl/cm$^2$. The CM with 200 μl/cm$^2$ gave a higher number of beating areas after 12 days differentiation.
Figure 9:
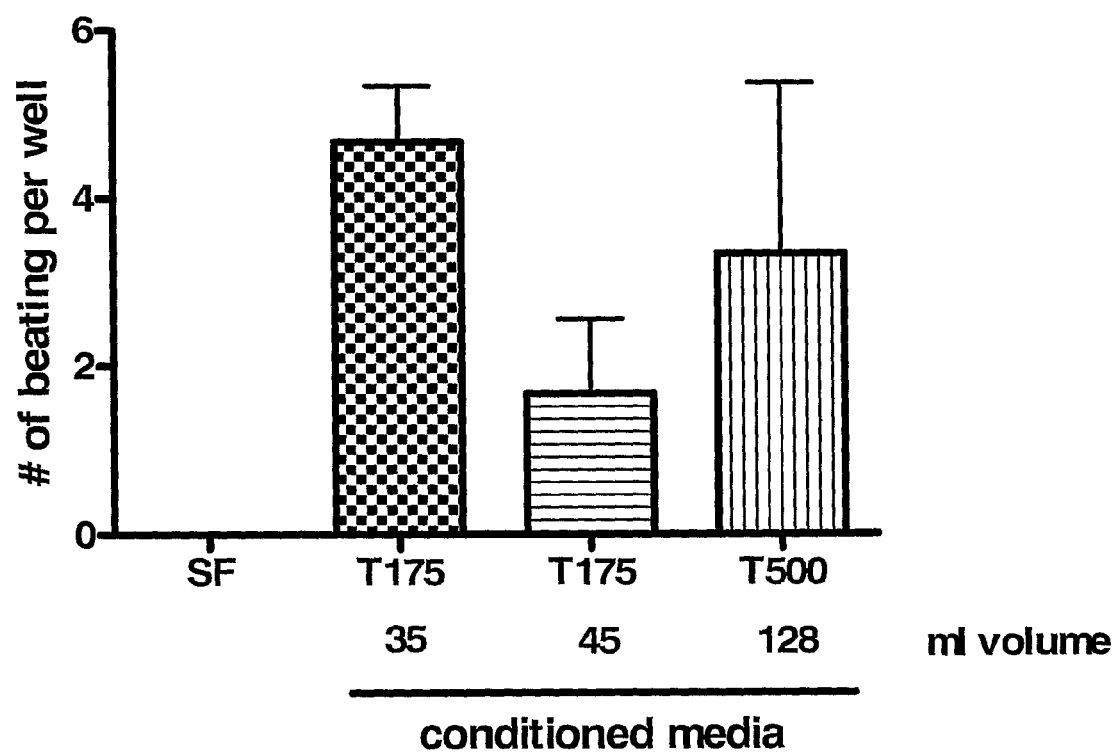
FIG. 9 shows a histogram showing no difference when using a T500 or a T175 flask for conditioning, both deliver around the same quality of CM. 200 μl/cm$^2$ serum-free hES medium gave a better result in this experiment than using 250 μl/cm$^2$ (45 ml per T175).

Conditioning volume: The volume of SF medium used for conditioning also affected the number of beating areas at day 12. Conditioning END2 cells with a volume of 200 μl/cm$^2$ gave the best result in cardiomyocyte differentiation (FIG. 8). To increase the volume of END2-CM production a change from T175 flasks to T500 flasks was tested to determine whether it would have an impact on the cardiomyogenic quality of the END2-CM (FIG. 9). There is no impact on END2-CM quality as long as the media volume stays in the range of 50-500 μl/cm$^2$.

Figure 10:
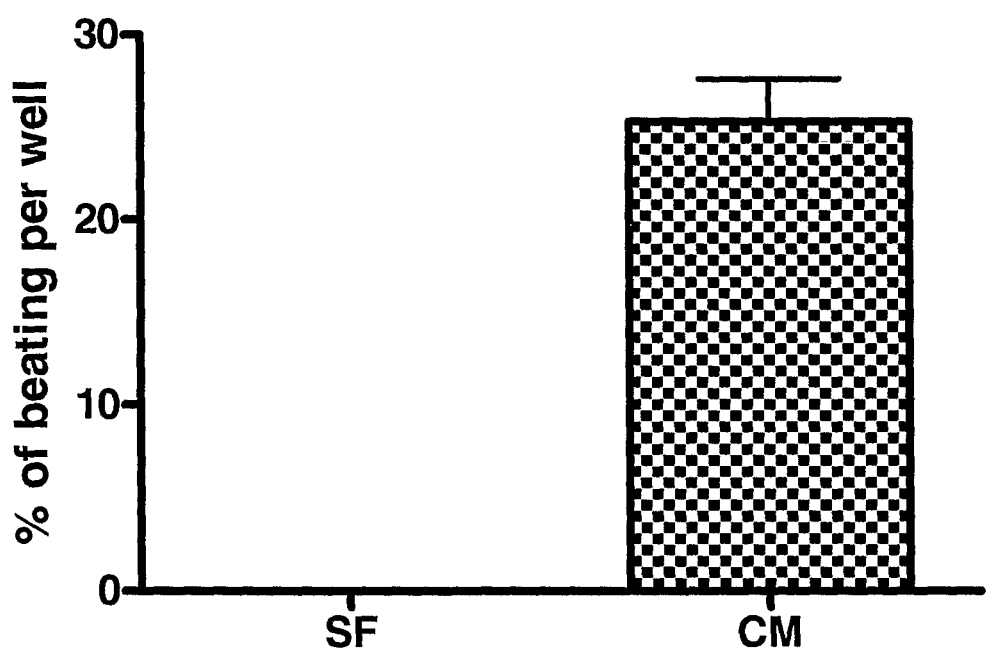
FIG. 10 shows that END2-CM prepared from late passaged END2 cells appears to be as effective at inducing beating EBs (cardiomyocytes) as earlier passage END2 cells in our culture system. Note the absence of beating EBs in the SF negative control.
Figure 11:
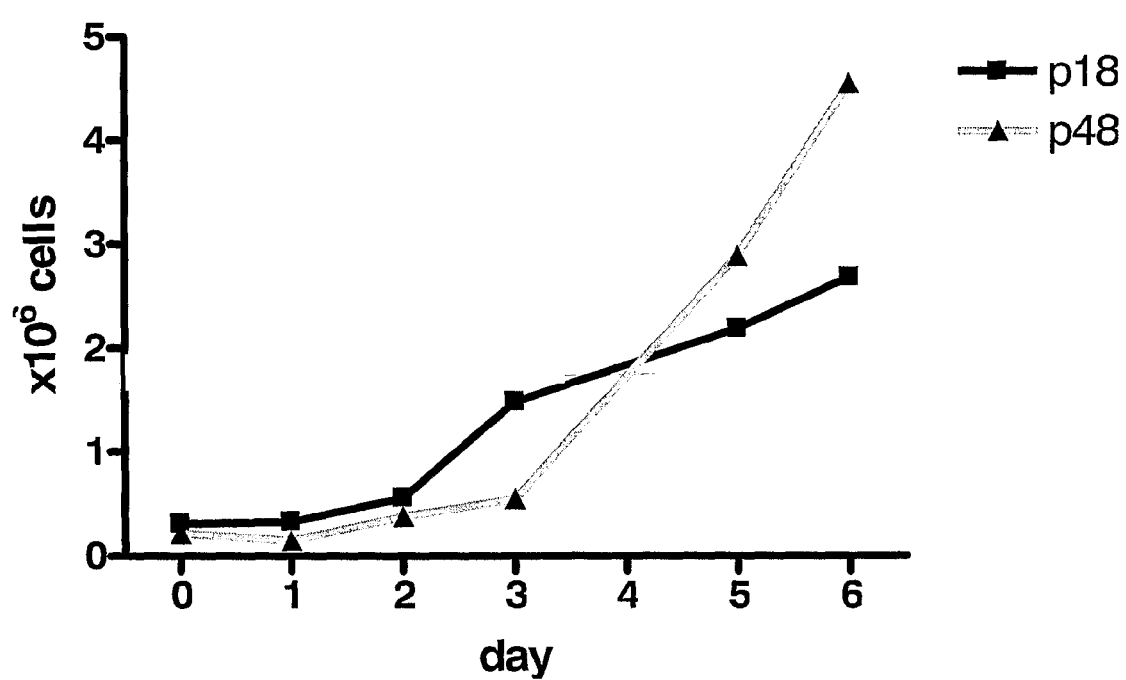
FIG. 11 shows late passaged END2 cells do not attach as well after being passaged (fewer cells at Day 3), but seem to divide faster from day four onward.

END2 passage number and the bioactivity of END2-CM: To extend the lifetime of our END2 stock the effect of END2-CM coming from late passaged END2 cells (FIG. 10) was examined. However, although the bioactivity is similar the growth characteristics of END2 cells may be changing after longer periods in culture when growth curves from early and late passaged END2 cells are compared (FIG. 11).

It is possible that cell numbers at the end of the 4 day conditioning period may differ and the END2-CM might be of different composition/quality. To reduce the number of variables in the experiments END2 cells were use up to a passage number of 40 or less even though the data in FIG. 10 suggests that the bioactivity of the END2 conditioned media is maintained.

Example 2

Cardiomyocyte Differentiation from hES Cultures Grown on Either Mouse or Human Feeder Cells or Under Feeder Free Conditions 1. Material and Methods (i) Culture of hES cells on feeder cells: hES cells were grown on mouse embryonic feeder cells see example 1. hES cell culturing on Mitomycin C (10 μg/ml, Sigma) treated human fibroblastic feeder cells (HF) was performed as follows. Human fibroblastic feeder cells CCD-919Sk were obtained from ATCC (CRL-1826). Cells were cultured in T175 flask in DMEM with 20% FCS, 2 mM L-Glutamine, 1× Insulin-Transferrin-Selenium, bFGF (10 ng/ml; Invitrogen) and antibiotics (Pen/Strep) to confluency and treated with Mitomycin C (10 μg/ml) for 3 hours. Cells were passaged with trypsin/EDTA (0.125% w/v; 50 mM respectively; Gibco) and seeded at a density of $4.7 \times 10^4$ cells/cm$^2$ in culture trays (Nunc). The CCD919Sk cells were equilibrated in hES culture medium for 24 h before the hES were seeded on the feeder cells.

hES were grown in hES medium on HF and passaged every 7 days. For passaging hES cells were either pre-treated with collagenase IV (Gibco) for 3 min followed by mechanical dissociation or without collagenase and collected after mechanical dissociation only. Harvested cells were then transferred to newly prepared feeder cells and split 1-in-4 up to 1-in-6, respectively. Enzymatically passaged cells were discarded after 20 passages and cells maintained by mechanical passaging only were newly adapted to the collagenase IV passaging method.

For all other methods applied see Example 1.

2. Results hES cell lines grown on mouse feeder cells (MEF) gave an average percentage of 5-18% of beating EBs per well when differentiated in END2-CM. There was no difference in the number of beating areas between manual passaged or enzymatically passaged hES cells. Enzymatically passaged hES cultures were used for the ease of experimental set-up. Incidence of spontaneous beating in the SF control medium was very low (<1%). Transferring EBs to serum containing medium after differentiating for 12 days in END2-CM also reduced the number of beating areas rapidly. Beating was maintained for a longer period of time (>365 days) when these conditioned EBs were maintained in serum-free DMEM following differentiation.

MEF based hES culture gave a consistent induction of cardiogenesis when exposed as EBs to END2 CM. However, the number of beating EBs varied widely between experiments with the levels of beating EBs accounting for between 5 and 18% of the total EBs conditioned in independent experiments.

When the maintenance of hES cells is done on a human fibroblast feeder cell (e.g. CCD-919Sk) instead of a mouse embryonic fibroblast feeder, the EBs formed from human feeder culture based hES culture reproducibly performed much better in the differentiation conditions used to form cardiomyocytes. This was apparent by the number of beating embryoid bodies which increased significantly (FIG. 12A) as well as the number of EBs with multiple beating areas. Furthermore, spontaneous beating in our unconditioned SF media control wells reduced to almost zero.

Figure 12A:
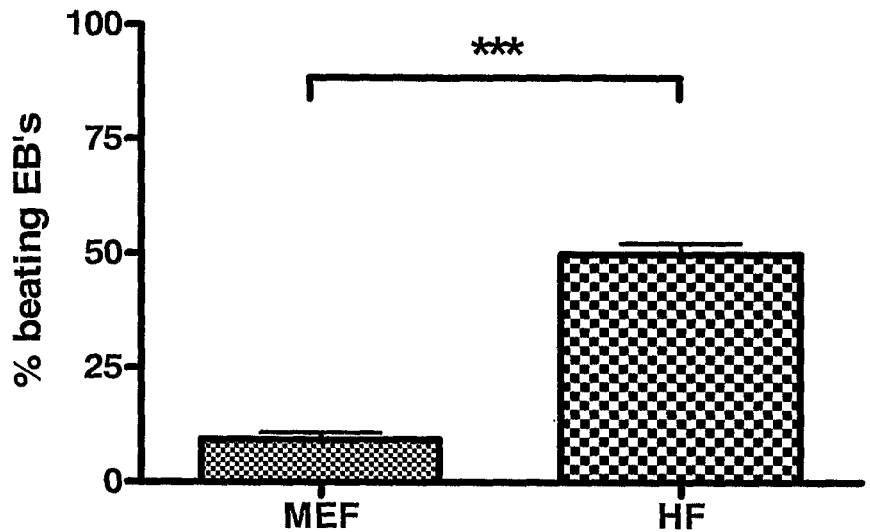
FIG. 12 shows a reproducible difference in cardiogenic response to END2-CM when hES cells are grown on human feeder cells (HF) with or without the addition of SB203580 compared to mouse feeders (MEF). EBs formed from hES cells grown on mouse (MEF, n=12) or human feeder (HF, n=19) cells were grown for 12 days in END2-CM (A). EBs formed from human feeder cells were grown for 12 days in END2-CM with (n=20) or without (n=19) the addition of 5 µM SB203580 (B, see text). Medium was changed every 3 days. EBs were scored for beating foci at day 12. (n=number of independent experiments).

EBs formed from hES cells maintained on human feeder (HF) cells resulted consistently in a much higher percentage of beating foci compared to EBs formed from mouse feeder cultured hES cells. The variations from different experiments based on HF cultures are in the range of 42-62% of beating EBs compared to the lower levels when hES cells maintained on MEFs were used (FIG. 12A).

Figure 13A:
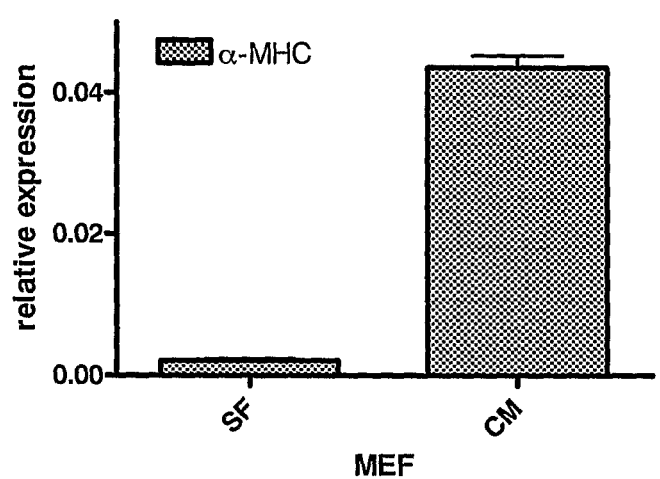
FIG. 13 shows a difference in the level of expression of cardiac marker genes between hES cells grown on HF and MEFs. After growing for 12 days in END2-CM EBs were collected for RNA extraction followed by qRT-PCR (s. below). a) RT-PCR for α-MHC on RNA collected from EBs formed from MEF based hES culture, b) RT-PCR on samples obtained from HF cultures, c) Combined FIG. 3 a) and b) in one single graph and log scale, difference MEF to HF.
Figure 13B:
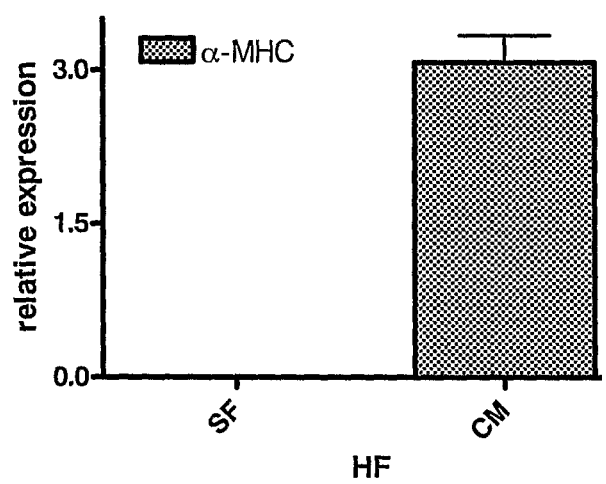
Figure 13C:
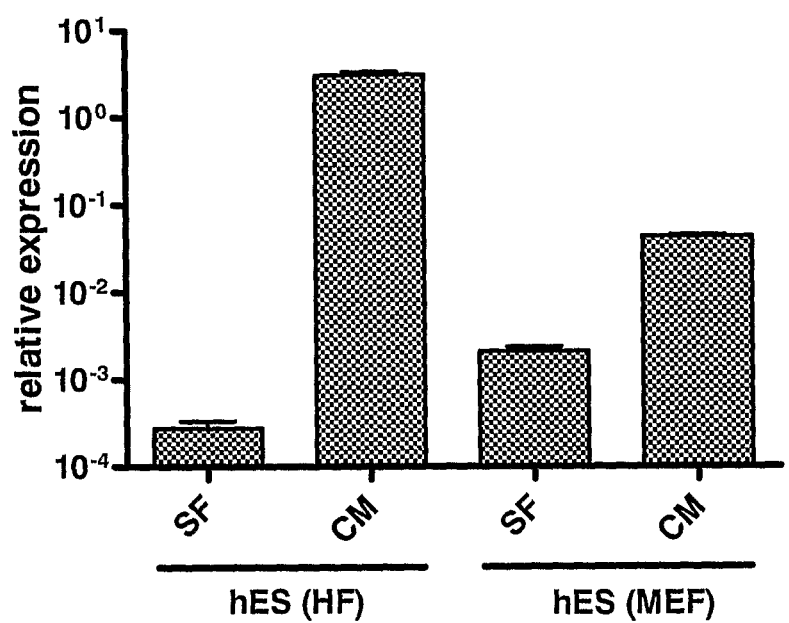

To determine if the number of beating areas induced was also reflected in the relative expression levels of cardiac markers quantitative real time PCR was performed with the cardiac marker genes α-MHC and ANF (ANF data not shown). qRT-PCR was performed in triplicates for each sample and a clear increase in the expression for all cardiac genes was observed by RT-PCR in cultures from HF derived EBs compared with those in coming from MEF (FIG. 13). All results were normalized against α-Actin using the $\Delta\Delta C_T$ method (19). Levels of α-MHC were up to 75 times higher in EBs formed from HF based hES cultures at days 12 of differentiation in END2-CM. ANF expression was also up-regulated in HF based experimental set-ups. In all cases ANF relative expression was lower than α-MHC expression but showed a similar change in expression levels when MEF based hES cells were compared with HF based hES cells for response to END2-CM.

Figure 6A:
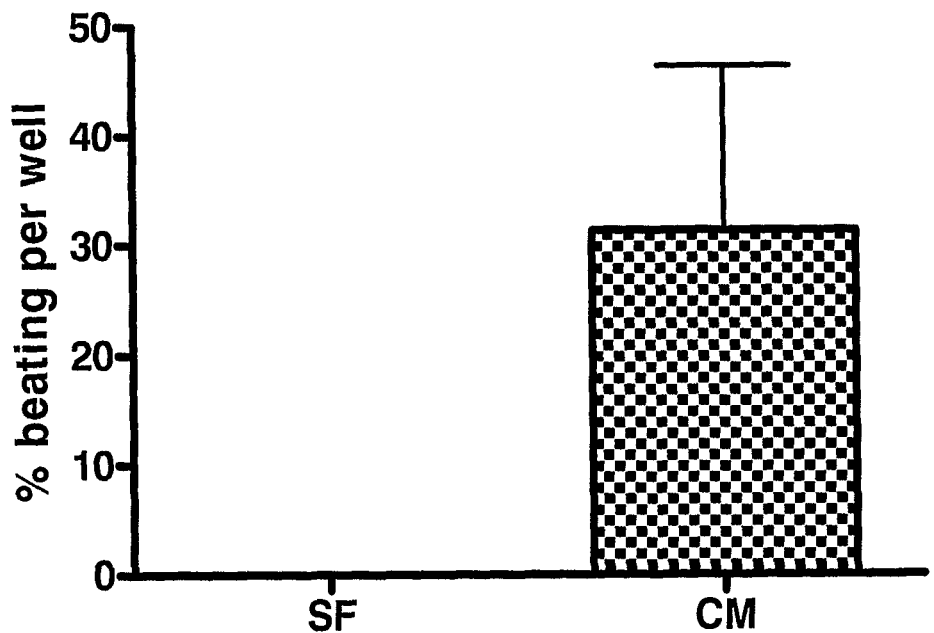
FIG. 6 shows an END2-CM response of hES cells cultured on fibronectin without the use of feeders. EBs were formed overnight in SF medium followed by 12 days in SF or CM. Medium was changed every 3 days. EBs were scored for beating foci at day 12 (A). RNA was extracted followed by qRT-PCR (B).

The END2-CM differentiation protocol was tested on hES cultures grown under feeder independent conditions. hES2 and hES3-GFP lines maintained on HF were adapted to grow in a feeder free culture system, based on a combination of fibronectin and high concentrations of bFGF ((20), modified). After a few weeks growing under feeder free conditions, the cells were subjected to the END2-CM differentiation protocol as described above (example 1; FIG. 6A).

Figure 6B:
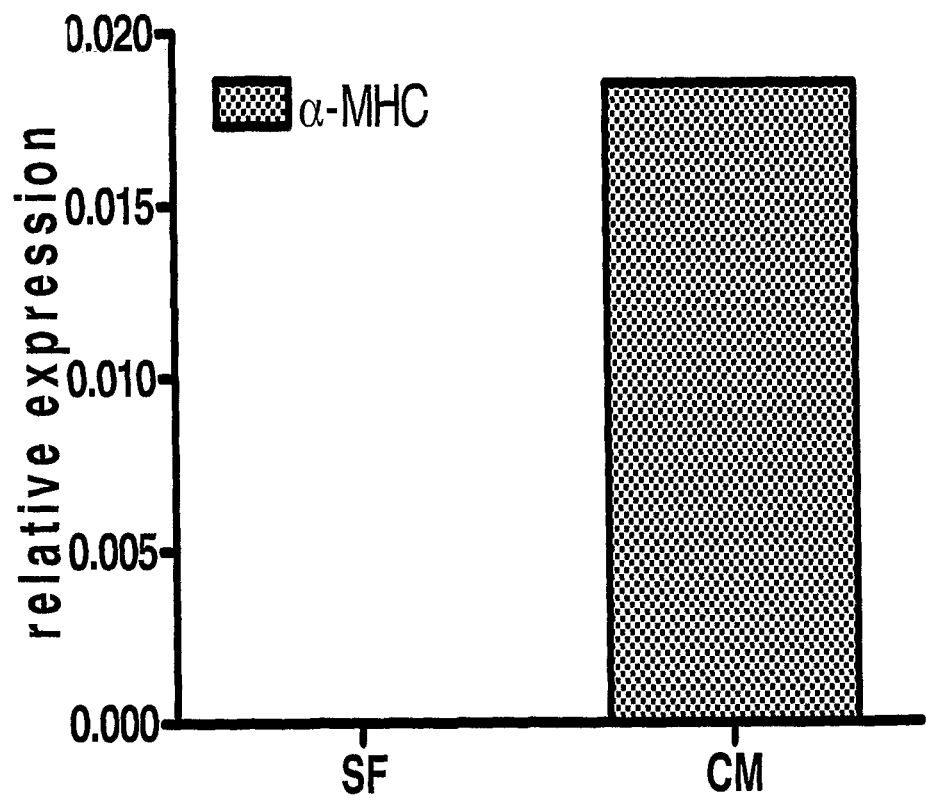

These hES cells also differentiated into cardiomyocytes with some EBs displaying multiple beating areas. The cardiac marker genes α-MHC and ANF were also up-regulated in EBs after 12 days exposure to END2-CM (example 1; FIG. 6B). Therefore, cardiogenesis was also observed from hES cells cultured in CM independent of growing the starting material in a feeder free based system, on mouse or human feeder cells. However, it is apparent that hES cells cultured and maintained on HF cells show a much better and more consistent response to the inducing factors in the END2 CM.

Example 3

Characterization of Cardiomyocytes Differentiation from hES Cell-Derived EBs Grown in Suspension Culture 1. Material and Methods
For hES culture on human feeder cells, see Example 2.
(i) PCR
PCR was performed as described under example 1. The samples were subjected to PCR amplification with human gene primers including:

Sox-1 (sense primer: AATTTTATTTTCGGCGTTGC; antisense primer: TGGGCTCTGTCTCTTAAATTTGT) and
Tbra (sense primer: AATTTGGTCCAGCCTTGGAAT; antisense primer: CGTTGCTCACAGACCACAG) and
SOX17 (sense primer: CAGAATCCAGACCTGCA-CAA; antisense primer: CTCTGCCTCCTCCACGAA) and
GATA4 (sense primer: TCCAAACCAGAAAACGGAAG; antisense primer: GTTGCTGGAGTTGCTGGAAG) and
Oct4 (sense primer: CAATTTGCCAAGCTCCTGA; antisense primer: CGTTTGGCTGAATACCTTCC). All reactions were run in triplicate.

(ii) Cytochemistry: The following antibodies were used sarcomeric Tropomyosin (clone CH1, Sigma), MF20 Hybridoma Bank, Iowa), MLC-2a, MLC-2v (both Synaptic Systems) and sarcomeric α-Actinin (Sigma) (21).

Paraffin sections: Beating EBs were collected and fixed for 15 min in 10% formalin at room temperature. EBs were then embedded in 1.5% agarose and dehydrated through 70% to 100% ethanol with a last incubation in xylene. The agarose block was then embedded in paraffin. 5 μm thick sections were cut in ribbons, floated on a warm water bath of 45° C., mounted on slides, and left to air dry at 37° C. overnight.

The next morning the sections were shortly incubated in xylene and rehydrated through a series of ethanol concentration ranging from 100% to 70%, followed by a wash in PBS. For antigen retrieval, the sections were exposed to a microwave oven in 10 mM citrate buffer. The slides were allowed to cool to room temperature, rinsed in PBS and used for staining.

Cryosectioning: About thirty to forty beating embryoid bodies (EBs) were collected and incubated in serum-free DMEM at 37° C. for at least 4 h before being transferred to a microtube and washed with 1 ml PBS$^-$ (Gibco). EBs were fixed in 4% PFA for 1 h at room temperature. Subsequently, the EBs were washed in PBS$^+$ and incubated overnight in distilled water and 25% sucrose (Sigma) at 4° C. on gentle rocking.

The next morning any traces of sucrose were removed by washing in PBS$^+$. EBs were then transferred to tissue freezing medium (Jung), snap-frozen in liquid and either sectioned immediately or stored at −20° C. or −80° C. until needed.

7 micron sections are cut at −20° C. using a cryostat CM3050S (Leica) and dried onto slides (SuperFrost Plus, Menzel-Glaser) at room temperature. The slides can be stored at −20° C. or −80° C. until needed for staining.

DAB staining: Slides were allowed to warm to room temperature before immersing them in PBS$^+$. Subsequently, the cells were permeabilised with 0.1% Triton X-100 for 10 min at room temperature. Slides were then washed 3× in PBS$^+$ and incubated in PBS/1% BSA (Sigma) for 30 mins at room temperature. Blocker was removed and cells were incubated with the respective primary antibody (Ms-Tropo CH1 (Sigma) at dilutions 1:1000 and 1:3000 diluted in blocker) at 4° C. overnight. Two slides were used as a negative control, either using the isotype control Ms IgG1 (Zymed, 1:1000) or PBS$^+$ as a blank.

Rest of the staining was performed according to the manufacturer's instructions (Vectastain Elite ABC Kit, Vector Labs). The slides were mounted in FluorSave (Calbiochem) examined under the microscope (Zeiss Axiovert 200M).

Immunohistochemistry: Fixed cells (or EBs) were rinsed trice in ice-cold wash buffer (20 mM Tris, pH 7.4, 150 mM NaCl, 0.05% Tween-20) and permeabilised with 0.1% TX-100 for 10 min at RT. Cells were rinsed again trice with wash buffer and incubated in blocking solution (10% goat serum). The respective antibody was diluted in blocking solution and incubated for 1 h at room temperature. Cells were then rinsed trice in wash buffer before incubated with the respective secondary antibody, rabbit anti-mouse (1:500, Zymed), for 1 h at room temperature in the dark. Slides were rinsed trice with wash buffer, 10 min each, before incubated for 5 min at room temperature with DAPI (1:5000, KPL). Cells were finally washed twice for 10 min before mounted with FluoroSave (Calbiochem).

All slides were analyzed on a Zeiss Axiovert 200M Microscope. Images were taken using an AxioCam (Zeiss) connected to the microscope.

For all other methods applied see previous examples.

2. Results

Figure 14:
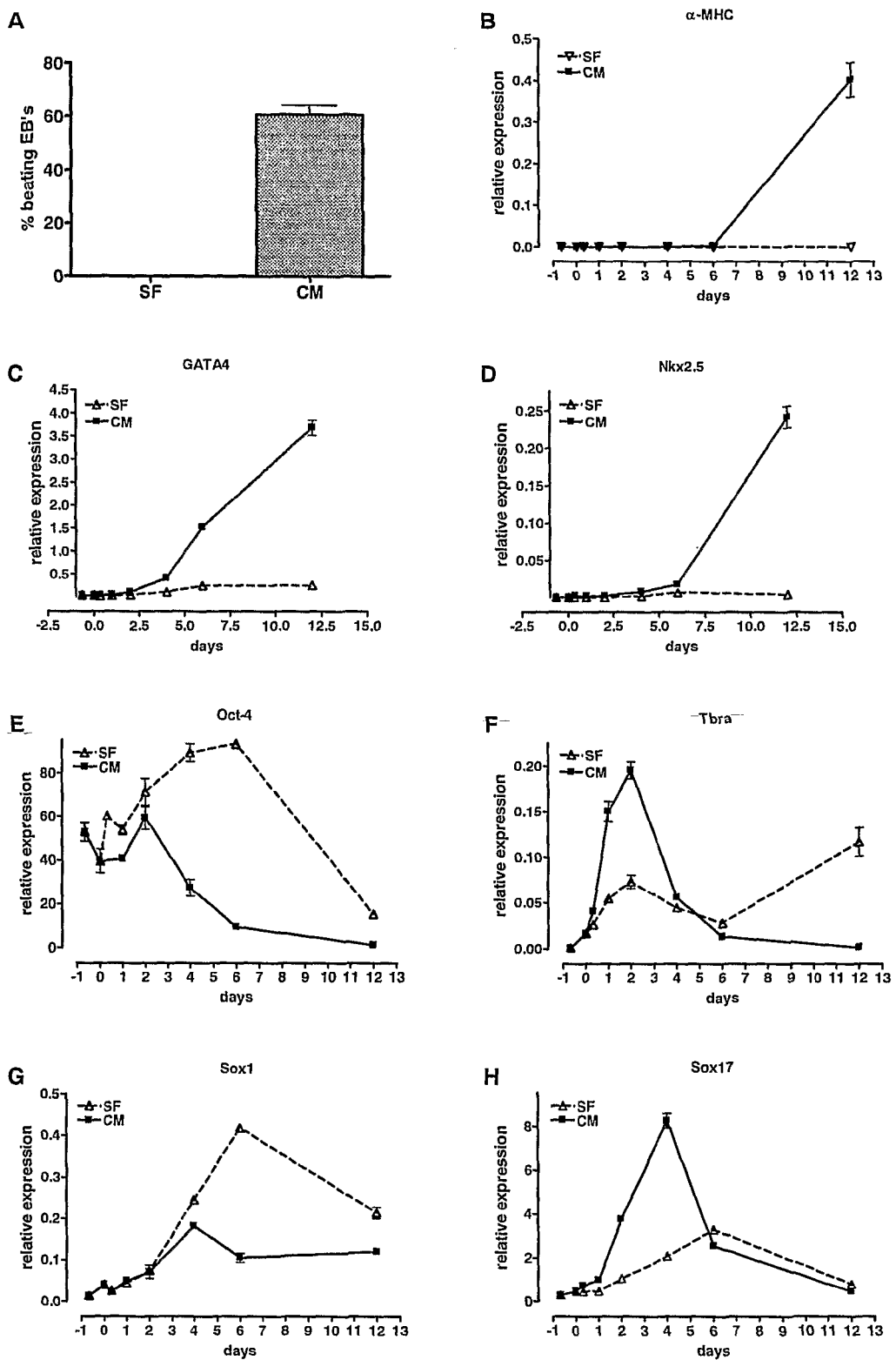
FIG. 14 shows an analysis of cardiomyogenic marker genes and differentiation markers in EBs over a period of 12 days by qRT-PCR. Expression profile of selected embryonic genes expressed in hES cells, early embryonic germlayers and cardiomyocytes in EBs over 12 days of differentiation in serum free DMEM or END2-CM. In this instance EBs were formed from hES3-GFP cells and grown in END2-CM over 12 days. (A) EB's were scored for beating foci at day 12. Samples for RNA extraction were collected from the undifferentiated hES culture (day −1), 12 hours after EB formation from in serum free medium (day 0), 8 hours after exposure to END2-CM, as well as after growing for 1, 2, 4, 6 and 12 days in END2-CM (3 independent wells for each time point). (B-H)

Early cell commitment in EBs growing in END2 CM: It is generally assumed that ES cell differentiation in vitro partially mimics the inductive events observed in the pre-implantation embryo in vivo (22). The expression of cardiomyocyte markers and general differentiation markers was examined in EBs grown in suspension at different time points. EBs were either grown over 12 days in END2-CM or SF medium, functioning as a non-cardiac inducing control medium. Samples for RNA extraction were taken from the original hES culture, 12 hours after EB formation in serum free medium, 8 hours after exposure to END2-CM, as well as 1, 2, 4, 6 and 12 days growing in END2-CM or SF (FIG. 14).

Differentiation under control conditions (SF) progressed slowly, the downregulation of the pluripotency marker Oct4, as well as Nanog and UTF1 (data not shown) was delayed compared to EBs differentiating in END2-CM. Mesoderm specific genes like Tbra (FIG. 14F) and Goosecoid (not shown) as well as endoderm specific markers like Sox17 were minimally expressed compared to EBs grown in END2-CM. Only the expression of Sox1 increased during the first 6 days in SF conditions. This could mean that EBs in SF medium are maintained longer in an epiblast like stage maintaining the expression of genes in the epiblast-embryonic ectoderm that are also expressed in undifferentiated hES cells before expressing ectodermal markers. Gene markers for general differentiation, like IGF-2 and HAND1 (23) were up-regulated under both culture conditions during early differentiation (data not shown).

Cell differentiation in EBs growing under END2-CM appeared to be less chaotic and random when compared to SF control conditions and showed synchronized expression patterns. Genes expressed in the mesoderm, like brachyury (marker of the primitive streak and peri-mesoderm (24)) and Mesp1 (marker for cardiac mesoderm (25)), were strongly up-regulated around day 3 when compared to the SF control data. This event was followed by the appearance of the early precardiac mesoderm lineage marker Nkx2.5 (26). Expression of Nkx2.5 was first detectable around day 4 and was significantly expressed at day 12 (FIG. 14D). Shortly after (around day 6) we detected the onset of α-MHC (FIG. 14B) and ANF (not shown) expression, markers of mature cardiomyocytes. EBs were also strongly expressing α-smooth muscle Actin (SMA) after day 4 (data not shown). It has been reported that SMA is present in embryonic and fetal but not in adult cardiomyocytes (27). No cardiac genes were expressed at day 12 under SF media conditions. Exposing EBs for the first 3 days to END2-CM only before changing back to SF medium was enough to induce cardiomyogenesis (Example 1, FIG. 3) suggests that commitment to the cardiac lineage was occurring within the first 3 days of culture in END2-CM. EBs growing in END2-CM are switching on genes of the primitive streak and starting to form cells mimicking mesoderm and endoderm of the pre-implantation embryo whereas EBs grown in SF medium alone do not develop beyond the epiblast stage, Characterization of cardiomyocytes obtained from hES cells derived EBs grown in suspension culture: To further establish the cardiac phenotype of cells that are induced from hES cells using END2-CM, EBs that were scored positive for beating areas and were isolated and cultured overnight on gelatin-coated chamber slides or collected for cryosections (see Material and Methods). For attached EBs, the EBs were then re-assessed for beating and the areas noted before fixation in paraformaldehyde followed by Immunohistochemistry for α-actinin and sarcomeric Tropomyosin.

Figure 15:
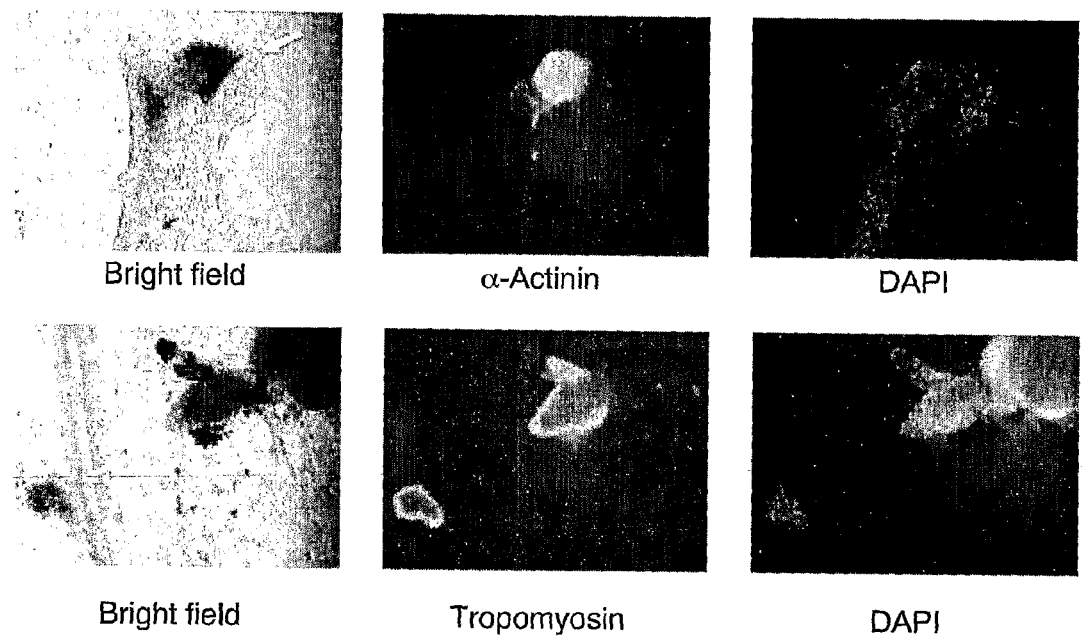
FIG. 15 shows whole mount immunohistochemistry on EBs that have been attached to cell culture plates. Beating EBs (originating from MEF maintained hES cells) stained for cardiac markers like Tropmyosin or α-Actinin. Arrows mark beating areas before fixation in PFA. The same regions stain positive after immunohistochemistry was performed.
Figure 16:
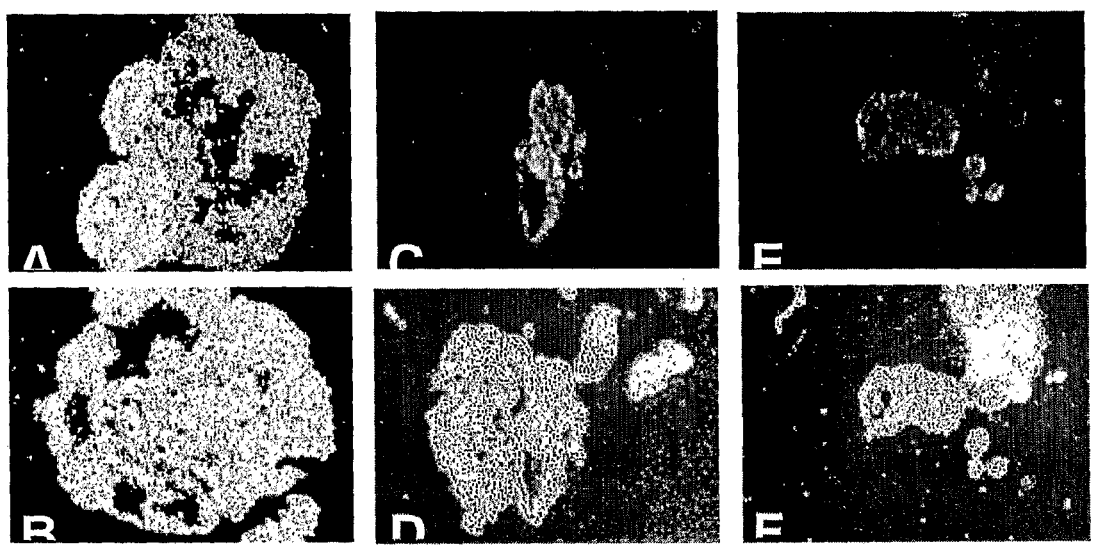
FIG. 16 shows serial sections through beating EBs. Beating EBs (from HF maintained hES cells) were prepared for cryosectioning and either stained for cardiac marker Tropmyosin following the DAP protocol (A) with the blank control shown in B or for the markers sarcomeric Tropomyosin (C) and or α-Actinin (E) in red and nuclei stained with DAPI (blue). The same field under brightfield in the panels D and F (s.Material and Methods, 10× magnification).

Following visualization it was apparent that the beating areas were positive for α-actinin and sarcomeric Tropomyosin (FIGS. 15 & 16).

To characterize the cardiomyocytes in our EBs further, we carried out immuno-fluorescence staining for sarcomeric proteins. EBs were grown in suspension for 12 days as described above and EBs with beating foci were either embedded in Paraffin (FIG. 17A) or dissociated to single cells and seeded on tissue culture plates or chamberslides. The hESC derived cardiomyocytes on paraffin sections stained positive for Tropomyosin, MLC-2a and sarcomeric MHC (MF-20). Areas which stained positive for cardiac markers overlaid in the serial sections showed here (FIG. 17A). MLC-2v was expressed in only a few cells when staining whole EBs. This most probably reflects the developmental state of the cardiomyocytes obtained at day 12 of differentiation. In the embryo, MLC-2a is initially expressed throughout the linear heart tube and becomes restricted to the atrial myocardium only later during development (28).

Day 12 EBs (around 60% displaying beating foci) were collected and dissociated using Trypsin. The single cell suspension was seeded on either 6 well tissue culture plates or chamber slides, forming a sub-confluent monolayer after 2-3 days (FIG. 17 B, C). Plated cardiomyocytes displayed sarcomeric striations when stained with α-Actinin or Tropomyosin, organized in separate bundles (FIG. 17B). We could observe a higher number of cells expressing MLC-2v in monolayered cardiomyocytes when compared to Paraffin sections of whole EBs. Cardiomyocytes were also positive for α-smooth muscle Actin (SMA). The morphology of cardiomyocytes grown in a monolayer ranged from small round to elongated, branched or triangular (the majority) cells of various sizes (FIG. 17B) with one nuclei or multi-nucleated cells. Mitosis was obvious in a few cardiomyocytes seeded on chamberslides or 6 well tissue culture plates. And we could observe cardiomyocyte proliferation (by quantification over Cytospin) in our suspension culture at least until day 28. EBs with beating foci stopped contracting in the presence of serum, but have been maintained beating EBs under SF conditions for more than a year (see above).

Example 4

Addition of a p38 MAPK Inhibitor, SB203580, Influences Lineage Fate in Differentiating EBs 1. Material and Methods hES differentiation in suspension culture: EBs were formed in ultra low attachment plates in SF medium over night. After over night incubation SF medium was replace by fresh SF medium or END2-CM. Factors such as SB203580 were added to the respective media at this time to test their effect on hES differentiation. Subsequent medium changes were performed every 3-4 days. Usually, cells were cultured over a period of 12-13 days.

Alternatively, EBs can also be formed by culturing hES directly in bSFS, END2-CM or other suitable media without prior incubation in SF media over night. Different types of culture vessels that support cell cultivation in suspension culture such as Petri dishes, spinner flasks or other types of bioreactors might be used (18).

Treatment with the p38 MAP kinase Inhibitor SB203580: p38 MAPK inhibitor SB203580 or [4-(4-Fluorophenyl)-2-(4-methylsulfinylphenyl)-5-(4-pyridyl)1H-imidazole] (Calbiochem) was dissolved in DMSO (13 mM stock solution) and added directly to the respective medium (SF or END2-CM) either during EB formation, during the first medium change or as indicated in the respective figures (see figures for final concentrations). Medium change was performed at day 3, 6 and 9 after EB formation.

For all other methods applied see previous examples.

2. Results

We tested various small molecules to improve cardiomyocyte differentiation in our differentiation protocol. Recently a number of small molecules have been identified that induce cardiomyogenesis in mouse EC cells (15). It had previously been reported that inhibition of p38 MAPK blocks cardiomyogenesis and commits cells to down the neurogenesis pathway in mouse ES cells (14,29). Another group showed an increased proliferation of neonatal cardiomyocytes after p38 MAPK inhibition (12). Surprisingly, when we added 5 □M of the specific p38 MAPK inhibitor SB203580 we observed an increase in the number of EBs with beating foci. This was only observed when the inhibitor was added early during differentiation, during or shortly after overnight EB formation. If we added the inhibitor after cardiomyocytes were already formed in the EBs (day 6 onwards), there was no effect on the number of beating foci (FIG. 18A) or the expression of α-MHC at day 12. This would suggest that the stimulation of proliferation of cardiomyocytes described by others can not fully explain what we observe in our differentiation system. The addition of SB203580 during the first 3 days of differentiation was enough to observe a remarkable increase in the number of beating foci per EB at day 12 (data not shown). The compound had also a positive effect on the size of the contracting area as well as the beating frequency of beating foci. In some instances we could observe beating EBs emerge in SF medium. However, the beating areas stayed smaller than their counterparts growing in END2-CM. The addition of vehicle (DMSO) alone had no positive effect on cardiomyocyte development (in accordance with (7)). EBs growing from the start in END2-CM with p38 MAPK inhibitor displayed an increased expression of cardiac markers at day 12 when compared to EBs grown in END2-CM alone (FIG. 18B). It was observed the same effect when adding another derivative of the p38 MAPK inhibitor (SB202190, FIG. 19).

Figure 18:
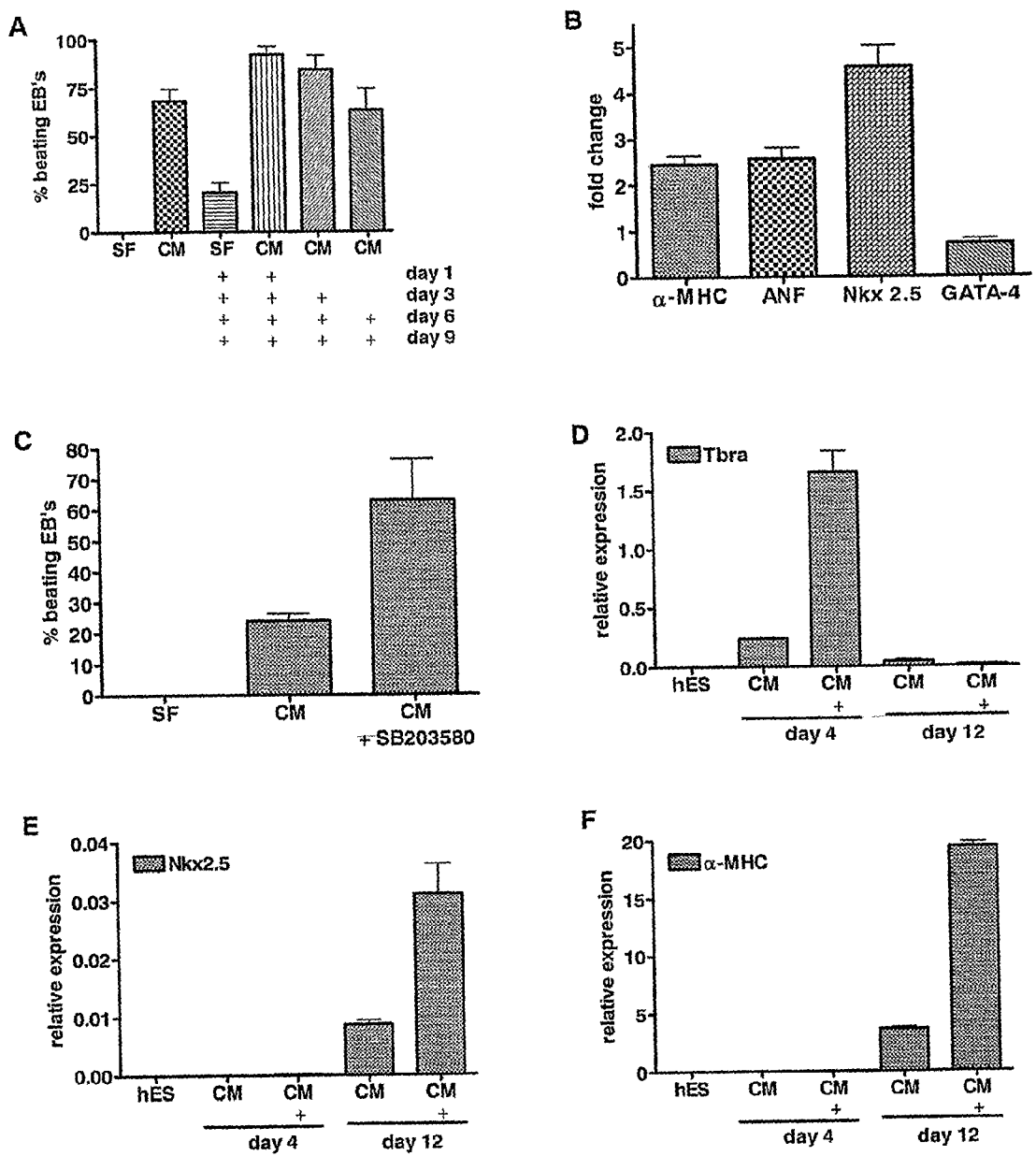
FIG. 18 shows the effect of cardiomyogenesis and cardiac marker gene expression in hES-derived embryoid bodies following treatment with SB203580. (A) EBs were grown in END2-CM and the END2-CM was supplemented with 5 µM of SB203580 during media changes as indicated. EB's were scored for beating foci at day 12. (B) RNA was extracted from EBs grown for 12 days in END2-CM with or without the addition of 5 µM SB203580. The fold change in cardiac marker expression was calculated (compared to END2-CM alone). (C) Cardiogenic effect of SB203580. EB's were scored for beating foci at day 12. Samples for RNA extraction were collected from the undifferentiated hES culture (hES), after growing for 4 and 12 days in END2-CM (3 independent wells for each time point). END2-CM was supplemented with 5 µM SB203580 (indicated by +). (D-F) The expression of Brachyury (Tbra), Nkx2.5 and α-MHC were examined by qRT-PCR.
Figure 19:
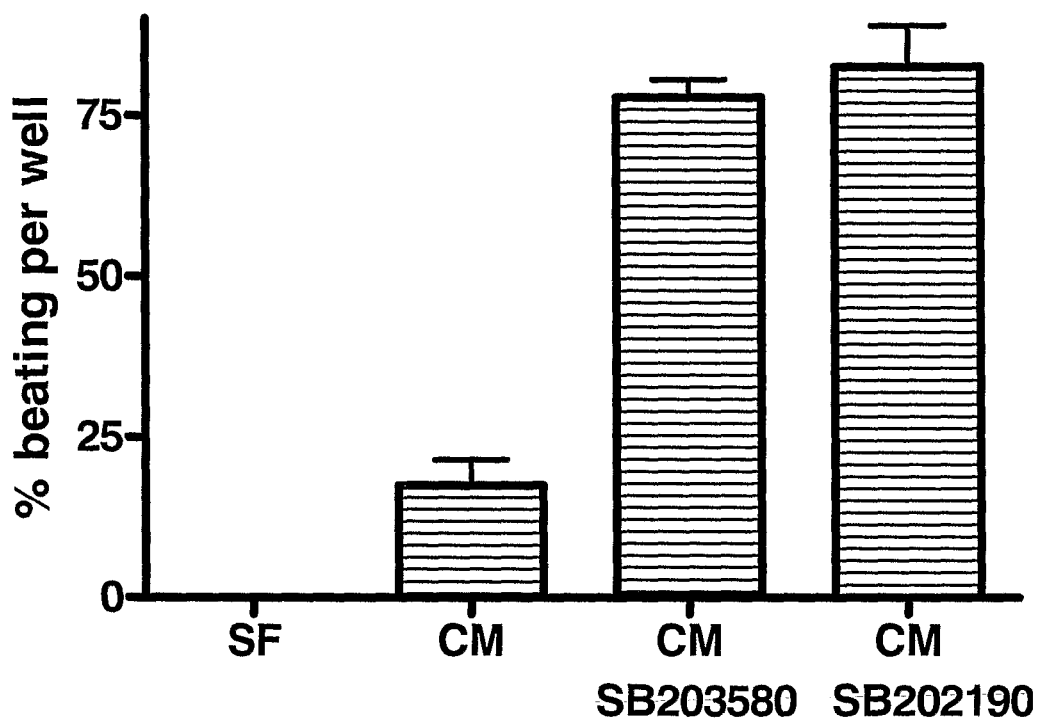
FIG. 19 shows a comparable cardiogenic effect of a different inhibitor of p38 MAP kinase activity (SB202190). EBs were formed over night in SF medium followed by 12 days in SF or CM. END2-CM was either supplemented with 5 µM of the p38 MAPK inhibitor SB203580 or SB202190. Medium was changed every 3 days. EBs were scored for beating foci at day 12.

Changes were checked in early gene expression during EB differentiation when adding the compound. A strong upregulation of Brachyury around day 4 was observed when cells are grown in the presence of the inhibitor. This would result in the formation of more mesoderm and therefore heart mesoderm. The higher expression of Tbra at day 12 was reflected in a higher expression of the cardiac markers Nkx2.5 and α-MHC at day 12 (FIG. 18 E-F).

Batches of hES culture being less responsive to the cardiac-inducing effect of END2-CM (percentage of beating EBs dropping below 50%) were sometimes encountered. However, in these cultures the cardiac-enhancing effect of SB203580 was even more pronounced, resulting in more than 60% of beating EBs (FIG. 18C).

Figure 12B:
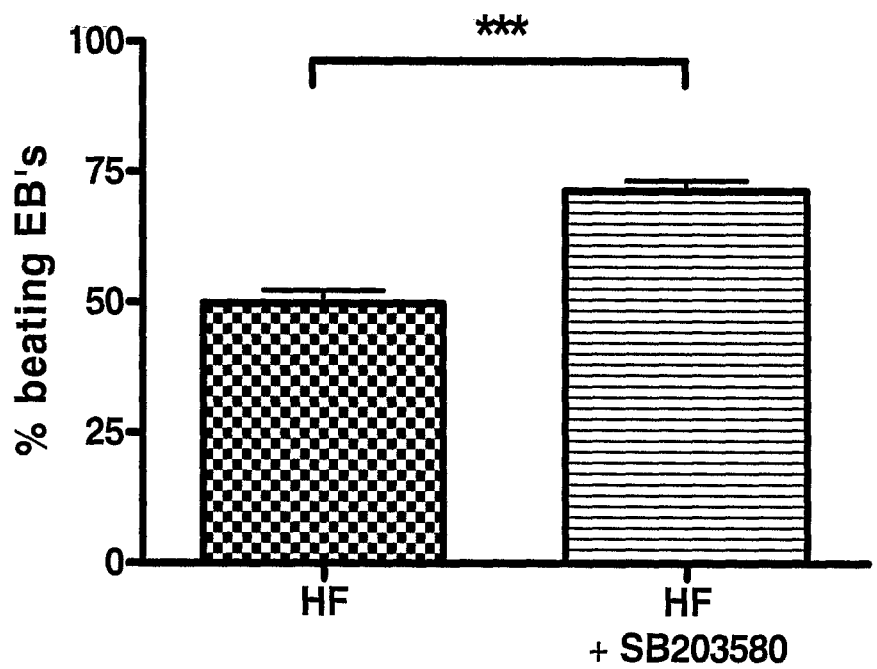

Over an extended number of experiments, the addition of SB203580 resulted consistently in a much higher percentage of beating foci compared to EBs growing in END2-CM alone. The percentage of beating EBs in the presence of 5 µM SB203580 is in the range of 60-87% compared to 42-62% in END2-CM only (Example 2, FIG. 12B).

The p38 inhibition at 5 µM in END2-CM did not induce expression of skeletal markers, like Myf5, endoderm markers, like Sox17 or neuroectoderm markers, like Sox1. Therefore the effect of the p38 MAPK inhibitor seems to be specific for the upregulation of genes confined to the primitive streak/mesoderm of the developing embryo that will then develop further into cardiac mesoderm.

Example 5

Quantification of Cardiomyocytes Grown in END2-CM or END2-CM Supplemented with 5 µM SB203580

1. Material and Methods (i) Quantification of cardiomyocytes after hES differentiation: The culture plates were scored for beating EBs 12-13 days after EB formation. Multiple beating areas on single EBs were not counted separately although this appearance was prominent upon visual inspection. The percentage of contractile EBs was evaluated as mentioned above.

To more accurately determine the number of cardiomyocytes in the differentiated cell population, EBs were collected, washed in PBS⁻ and incubated with 0.05% Trypsin for 5 min at 37° C. Cell clumps were triturated and incubated for another 5 min at 37° C. Trypsin activity was inactivated with serum containing media and cells were collected via centrifugation at 2500 rpm for 4 min at 4° C. The cell pellet was resuspended in PBS for cell count and cytospun onto glass slides at 500 rpm for 5 min at low acceleration using $1 \times 10^5$ cells. Cells were stained immediately (see previous example) and a cell count performed.

For all other methods applied see previous examples.

2. Results

Figure 20:
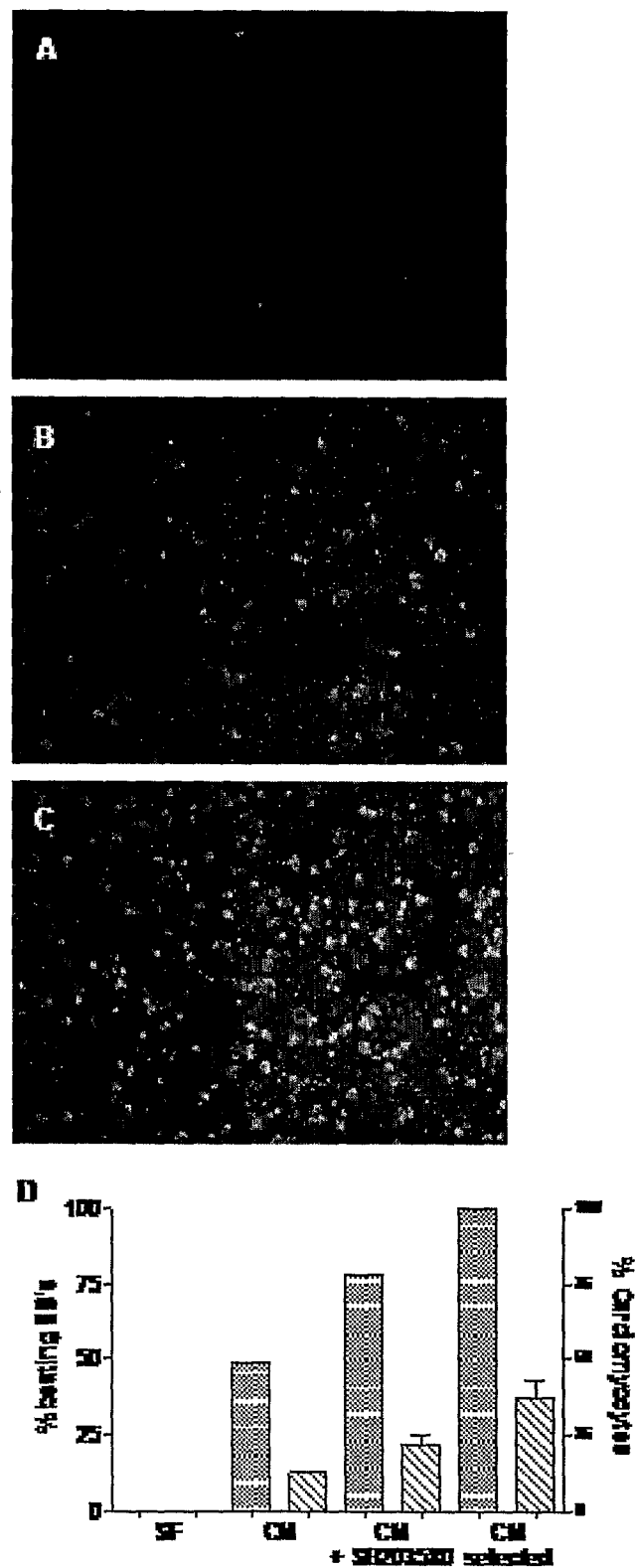
FIG. 20 shows quantification of cardiomyocytes in EBs grown in SF media, END2-CM or END2-CM supplemented with SB203580. (A-C) hES cells were differentiated over 12 days in END2-CM and beating EB's were dissociated with Trypsin before transferred to glass slides for Cytospin immunohistochemical analysis. Adherent cells were fixed and stained by Immunohostochemistry using the MF20 antibody and cell nuclei were counterstained with DAPI. (D) Displayed is the percentage of beating EBs (left Y-axis) against the percentage of cardiomyocytes (right axis). Manually selecting for beating EBs only (column pair on the right) further increased the percentage of cardiomyocytes in the cell population to almost 40%.

Calculating the percentage of beating EBs or the relative expression of cardiac markers provides only a very rough estimate of the efficiency of cardimyogenesis in our differentiation process. To obtain a more accurate number of actual cardiomyocytes present in EBs at day 12 EBs were dissociated using Trypsin. A cell suspension of $1 \times 10^5$ cells was spun on a slide using a Cytospin and immunohistochemistry was performed using MF-20. EBs grown in END2-CM and displaying around 49% of beating EBs at day 12 yielded around 11.8% of cardiomyocytes while EBs grown in END2-CM supplemented with 5 µM SB203580 (78% beating EBs) yielded 21.7% cardiomyocytes (FIG. 20). Normalized to the total cell number at day 12 for each condition, $0.84 \times 10^6$ cells/well for END2-CM and $1.16 \times 10^6$ cells/well for END2-CM supplemented with SB203580, a 2.5 fold increase was obtained in the total number of cardiomyocytes when SB203580 was added. Performing a simple enrichment step by removing non-beating EBs could further increase the yield to almost 40% cardiomyocytes of the total cell population (FIG. 20D). Cultures growing in medium supplemented with 5 µM SB203580 had consistently yielded higher cell numbers after 12 days of differentiation.

Example 6

Concentration Dependent Stimulation of Cardiac Differentiation by p38 Inhibition 1. Material and Methods For hES culture on human feeder cells, see Example 2. For Immunohistochemistry performed here, see example 3. H&E staining on Paraffin sections was performed at the BSF facility (Biopolis).

For all other methods applied see previous examples.

2. Results

Figure 21:
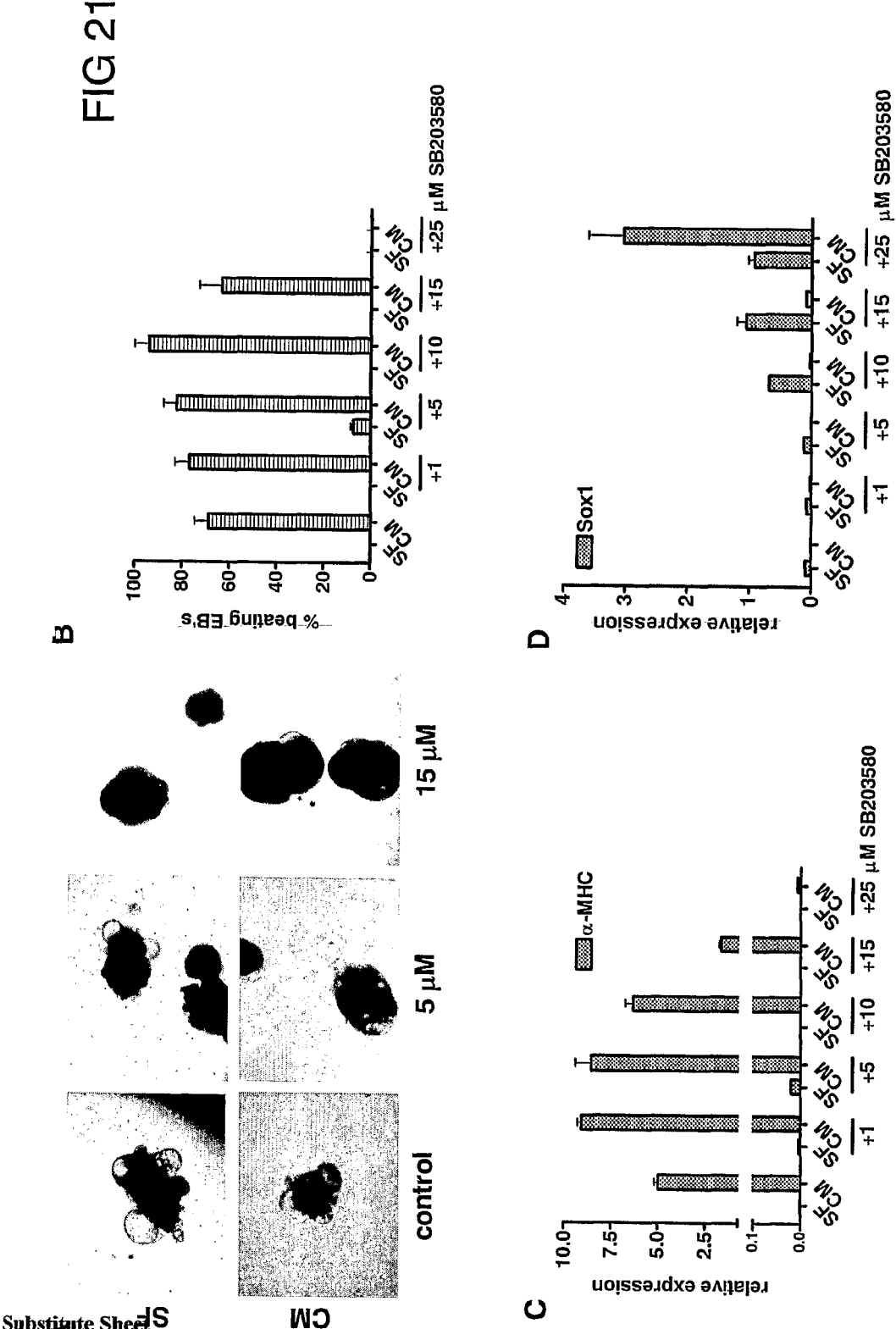
FIG. 21 shows concentration dependent effect of SB203580 on hES differentiation. END2-CM was supplemented with various concentrations of SB203580 (ranging from 1 to 25 µM) for 12 days of differentiation. (A) EB's were scored for beating foci at day 12. RNA was extracted and the mRNA expression of the cardiac marker α-MHC (B) and the neuron-precursor marker Sox1 (C) was analyzed by Real Time PCR. (D) Morphology of EBs grown for 12 days in END2-CM with or without the addition of SB203580.
Figure 22:
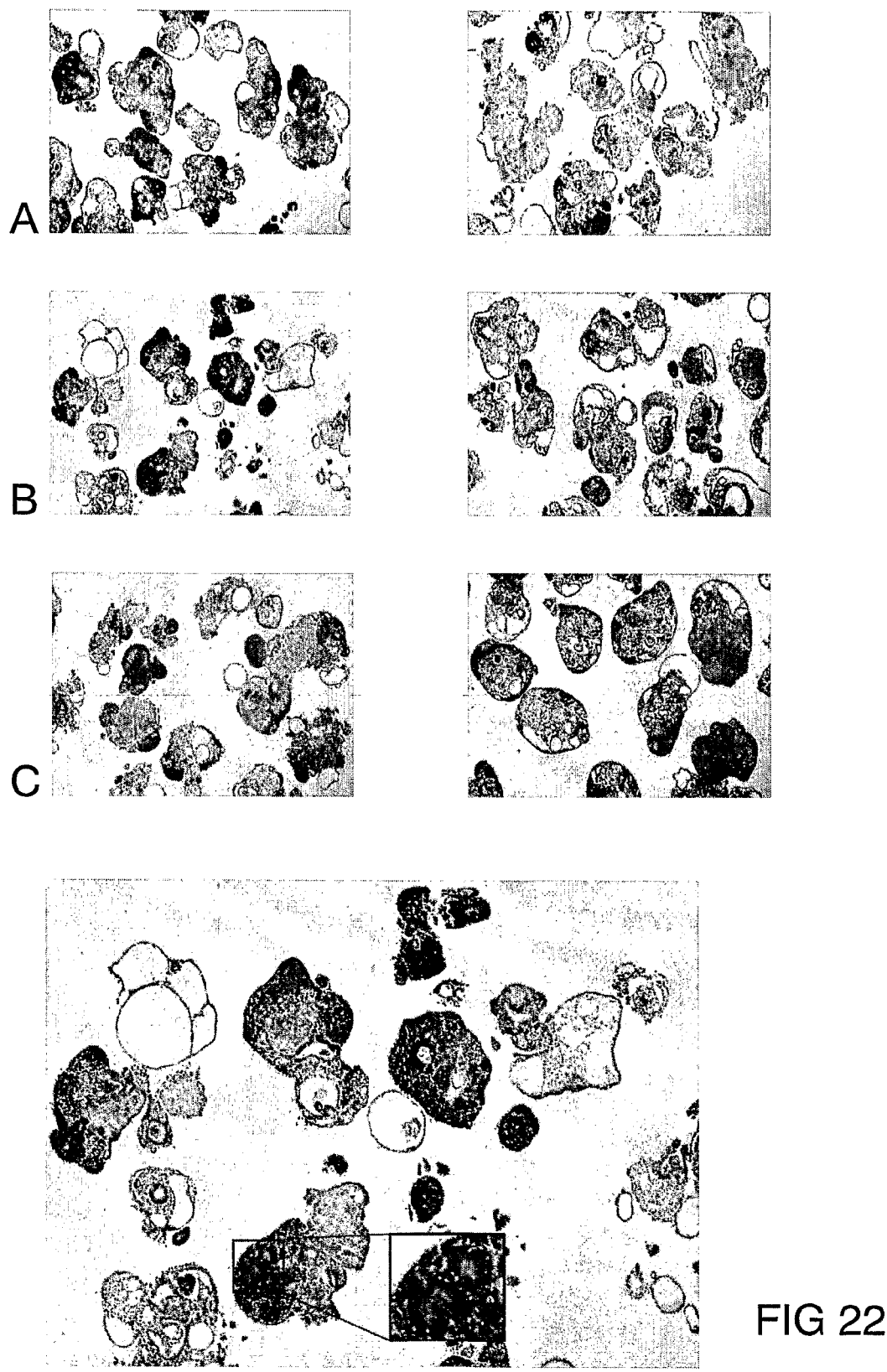
FIG. 22 shows EBs grown in END2 CM alone or in CM supplemented with either 5 or 20 µM SB203580 for 12 days. EBs were collected at day 1, day 3 and day 12, embedded in paraffin, sectioned and H&E staining was performed (see text).

The dose response of cardiac induction by p38 MAPK inhibition was investigated. Aouadi et al has recently published that concentrations of 10 µM of the p38 MAPK inhibitor PD169316 prevented cardiomyogenesis in mouse ES cells and induced neurogenesis (29). The END2-CM was supplemented in a range between 1 and 25 µM of SB203580 over a period of 12 days (FIG. 21). The first observation was a change in the morphology of EBs. When exposed to higher concentrations of the p38 MAPK inhibitor SB203580 EBs are more compact and do not form epithelial visceral endoderm, normally observed as large fluid-filled cysts (FIG. 21A). Beating foci were shifting from the surface to the inside of the EB structure. There was an increase in the number of beating foci up to a concentration of 10 µM of SB203580 when compared to non-supplemented END2-CM (FIG. 21B). Beating declined when the dosage was increased to 15 µM or more of SB203580 and there was no beating detectable at 25 µM. Surprisingly, beating foci were detected on EBs grown in SF supplemented with 5 µM of SB203580. Beating areas were smaller compared to beating foci of EBs growing under END2-CM. Similarly, the expression of α-MHC declined when the concentration of the p38 MAPK inhibitor went over 10 µM in END2-CM and was barely detectable at the highest concentration (FIG. 21C). However, at the higher concentrations the formation of rosette like structures in EBs were observed and checked for neuronal marker expression (FIG. 22). Sox1, one of the earliest expression markers in neurogenesis, marking the developing neuro-ectoderm, was upregulated in SF from 10 µM onwards and significantly expressed in END2-CM supplemented with 25 µM of SB203580 (FIG. 21D). Therefore, concentration dependent inhibition of p38 MAPK inhibition seems to induce different lineages in the EB gastrulation-event. These observations here would indicate that a dose dependent effect of SB203580 modulates the formation of germ layer lineages from hES cells with a low dosage shifting differentiation down the mesoderm/cardiac mesoderm pathway while a strong inhibition of the p38 MAPK pathway is inducing neuroectoderm.

Effect of p38 MAP kinase inhibitor on the appearance of a Neural Progenitor population: As it was previously noted that using the inhibitor SB203580 in SF medium was promoting the formation of neural progenitors in EBs it was also apparent that higher concentrations of inhibitor that completely blocked induction of beating EBs formed in END2 CM (FIG. 21A) that morphological uniform neuroepithelial EBs with clear rosette structure formed at higher doses of the inhibitor (>5 µM-25 µM) (FIGS. 22 & 23). Examples are given in FIG. 22:

(22A) SF control: Larger EBs consist mostly of loosely packed areas which might be high in extracellular matrix. EBs are cystic and display small areas of tightly packed cells. CM control: Large areas of loosely packed cells surrounded by extracellular matrix take up most of the bigger EBs. Some glandular structures are visible.

(22B) SF+5 µM SB203580: Again areas of large, loosely packed cells maybe smaller than in the control EBs. Rosette-like structures are obvious. CM+5 µM SB203580: More glandular structures appear and some rosette-like structures are obvious.

(22C) SF+20 µM SB203580: The EBs are similar in appearance to SF+5 µM SB203580, except that the EBs are noticeably larger. CM+20 µM SB203580: The cells are more densely packed and organized. More rosette-like structures are detectable and the EBs are less cystic.

EBs have grown progressively bigger in size from day 1 to day 12. In SF control, the morphology of EBs did not change much throughout the 12 days of differentiation. EBs in SF+20 µM SB203580 are significantly more compact than in SF control even as early as day 1. Between day 1 and 3, EBs in SF+5 µM SB203580 are not very different in morphology. Rosette-like structures only appear at day 12. Distinctive structures in EBs in SF+20 µM SB203580, CM+5 µM SB203580 and CM+20 µM SB203580 are visible from day 1, whilst in CM structures are only obvious at day 3. There are already considerable differences in EB morphology from day 1 onwards.

It is clear that after treatment with SB203580 the RNA expression of the neuroectodermal marker is increased in both SF and END2-CM (depending on the concentration see above). This occurs at much lower concentrations in SF conditions (10 µM) than in EBs cultured in CM (25 µM) possibly due to the propensity of hES cells to form neural progenitors under serum free conditions (30). However, at higher concentrations of SB203580 in END2-CM the number of beating EBs observed dropped dramatically with a concomitant increase in the expression of Sox-1 as well as down regulation of cardiac markers.

Example 7 p38 MAPK Inhibition is Modulating the Appearance of Germ Layer Lineages in a Concentration Dependent Manner in Differentiating hES Cells 1. Material and Methods:

For hES culture on human feeder cells, see Example 2.

PCR was performed as described under example 1. The samples were subjected to PCR amplification with human gene primers including MESP1 (sense primer: GACGTGCTGGCTCTGTTG; antisense primer: TGTCACTTGGGCTCCTCAG).

For all other primer and other methods applied see previous examples.

2. Results

Figure 24:
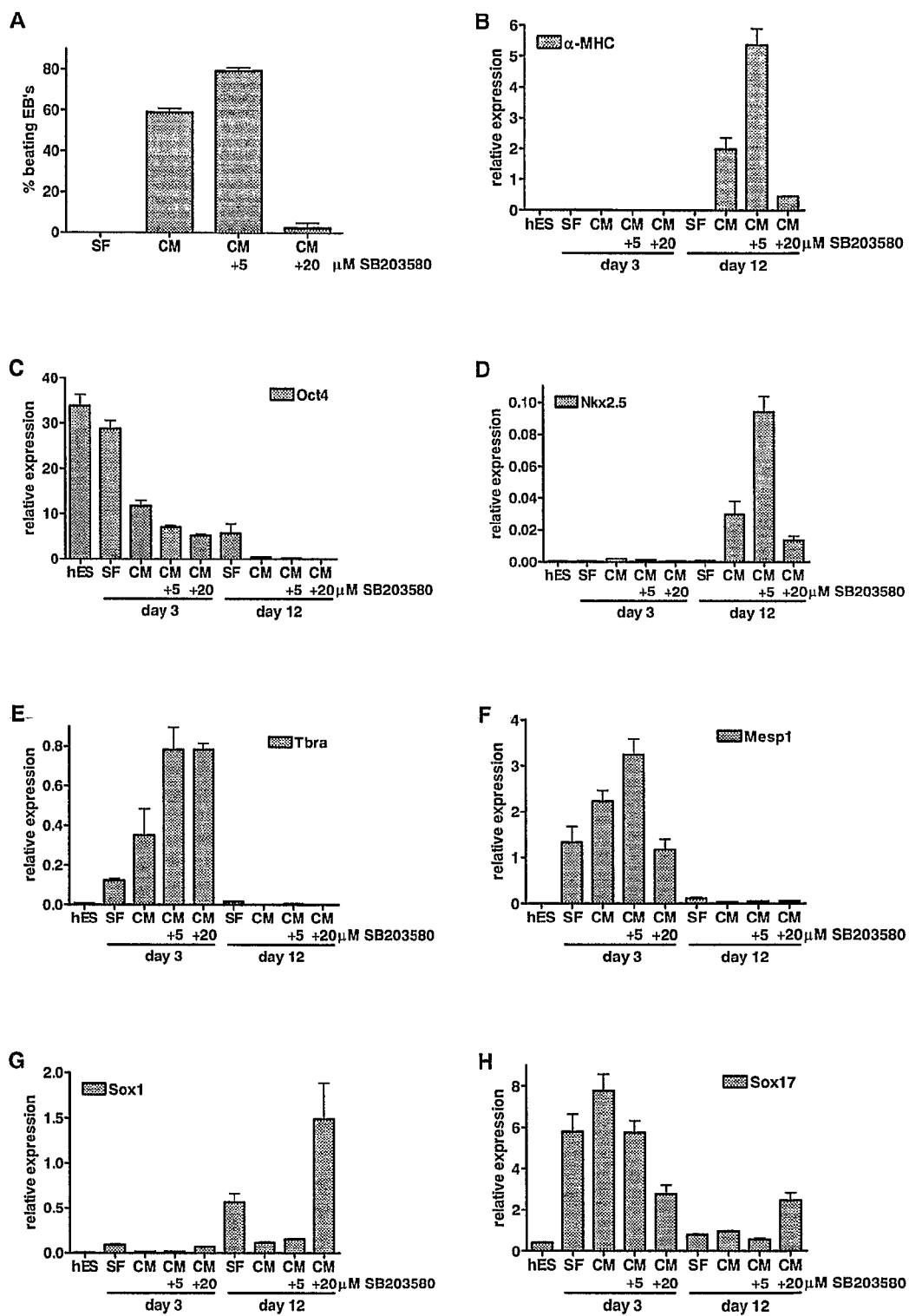
FIG. 24 shows an effect of SB203580 on early differentiation in embryoid bodies. EBs were grown in END2-CM alone or in END2-CM supplemented with either 5 or 20 µM SB203580 for 12 days. (A) EB's were scored for beating foci at day 12. (B) Samples for RNA extraction were collected from the undifferentiated hES culture (hES), after growing for 4 and 12 days in END2-CM (3 independent wells for each time point). Cardiomyocyte specific genes and differentiation markers were examined by Real Time PCR.

To investigate the effect of p38 MAPK inhibition on lineage commitment in EBs we stimulated EBs with 5 or 20 µM of SB203580 in END2-CM and checked for mRNA expression of different lineage markers at day 3 and day 12. Again, 20 µM SB203580 almost completely suppressed the formation of beating foci at day 12, while the addition of 5 µM increased the number of beating foci observed at day 12 when compared to END2-CM alone (FIG. 24A). Visual observation of beating foci was confirmed by the expression of α-MHC at day 12 (FIG. 24B). The lower concentration increased α-MHC expression as seen before, while the highest concentration reduced the expression of precardiac mesoderm (Nkx2.5) and cardiac marker genes. The expression of Nkx2.5 mimicked the expression profile of α-MHC (FIG. 24D).

Interestingly, Brachyury was upregulated under both p38 MAPK inhibitor concentrations (FIG. 24E). Brachyury is expressed in both, the node and early mesoderm and expressing cells give rise to mesoderm but also cells of the endodermal lineage (31). Mesp1 is expressed in cardiac mesoderm and plays an essential role in cardiac morphogenesis (25). Mesp1 was higher expressed in low concentrations of SB203580 and expressed at a level comparable to EBs grown in SF medium at higher concentrations of SB203580 (FIG. 24F). As seen in the previous experiment (FIG. 21) the expression of Sox1 is strongly upregulated in EBs exposed to high concentrations of the compound (FIG. 24G). A marker of early endoderm formation, Sox17 is also higher expressed at day 12 under high concentrations of the p38 MAPK inhibitor (FIG. 24F). This might indicate that under these conditions more mesendoderm is formed but differentiation down the cardiac-mesoderm, a more posterior primitive streak population is blocked.

It is therefore demonstrated that p38 MAPK may exert different roles during the differentiation of hES cells to various embryonic germ layer derivatives depending on the level of inhibition/activation and duration. These results suggest that p38 MAPK helps to modulate ES cell commitment during early gastrulation events.

Example 8

Stimulation of Cardiac Differentiation and Cell Proliferation by Addition of SB203580 into bSFS 1. Material and Methods For hES culture on human feeder cells, see Example 2.

(i) Culture media: Defined basic serum free medium (bSFS): DMEM supplemented with 1×MEM non-essential amino acids (Invitrogen), 2 mM L-Glutamine (Invitrogen), 0.0055 mg/ml Transferrin (Roche), 5 ng/ml sodium Selenite (Sigma), 0.1 mM β-mercaptoethanol, with or without Penicillin/Streptomycin (Invitrogen).

For all other methods applied see previous examples.

In this experiment the effect of SB203580 (SB) and Acetic Acid (AA) on cardiac induction when compared to END2-CM and a fully defined media bSFS was investigated. hESC were differentiated as EBs in suspension culture as described above. Readouts were performed on day 13: the percentage of beating EBs was defined, the average cell number per well was counted via a cytometer after EBs dissociation with trypsin, the percentage of cardiomyocytes was divined via cytospin followed by cardiomyocyte specific anti α-Myosin Heavy Chain stain (MF20 antibody), and RNA was harvest for qRT-PCR. Percent of beating EBs per well, cardiac α-Myosin Heavy Chain (α-MHC) expression relative to α-Actin (Actin), and percent of cardiomyocytes in the differentiated cells is presented in FIGS. 25A, B, and C respectively. The average total number of cells per well observed on day 13 is shown in Table 2 below.

Looking at the percentage of beating EBs on day 13 (FIG. 25A) we have observed that the addition of SB203580 at a 5 μM final concentration resulted in a 2-5 fold higher percentage of beating EBs in CM or in bSFS media, respectively. Addition of AA into bSFS at a 0.5 μM or 5 μM final concentration resulted in about the same percentage of beating EBs as in bSFS alone, with a slide increase at a 5 μM AA concentration. Addition of 5 μM SB203580 in combination with 0.5 μM or 5 μM AA in bSFS resulted in an up to 2 fold increase of the percentage of beating EBs compared to the respective AA concentration in bSFS alone, but the percentage of beating EBs was below the addition of 5 μM SB203580 into bSFS only.

The expression of cardiac α-MHC relative to α-Actin (FIG. 25B) is strongly indicating that the proportion of cardiomyocytes in the differentiation cultures was about 2-6 fold higher when SB203580 was added at a 5 μM final concentration in CM or bSFS respectively. Addition of AA into bSFS at a 0.5 μM concentration resulted in about the same relative expression of α-MHC as in bSFS alone; a slide increase at a 5 μM AA concentration was observed. AA at a 0.5 μM concentration in bSFS resulted in about 2 fold increase in relative α-MHC expression. Of note, addition of 5 μM SB203580 in combination with 0.5 μM or 5 μM AA in bSFS resulted in a 2-3 fold increase in relative α-MHC expression over 5 μM SB203580 alone and a 5-10 fold increase over the cardiac inductive effect of 0.5 μM or 5 μM AA alone, respectively. This clearly demonstrates that SB203580 has a strong inductive effect on cardiomyocyte formation in different media at the respective concentration. This effect is even when SB203580 is combined with AA at respective concentrations.

The percentage of cardiomyocytes in the cultures shown in FIG. 25C underscores the results observed via scoring beating EBs (FIG. 25A) and relative cardiac α-MHC expression (FIG. 25B). The addition of 5 μM SB203580 into END2-CM slightly elevated the percentage of cardiomyocytes but the addition of 5 μM SB203580 into bSFS almost tripled the proportion of cardiomyocytes. The addition of 0.5 μM or 5 μM AA in bSFS slightly increased the proportion of cardiomyocytes; but the addition of 0.5 μM and particular 5 μM AA in respective combination with 5 μM SB203580 in bSFS resulted in the highest proportion of cardiomyocytes in this experiment.

Table 2 is presenting the average cell number per well on day 13; note that all wells were inoculated from the same cell suspension initially to ensure an even distribution of cell number in all wells at the initiation of the differentiation. The addition of SB203580 at a 5 μM final concentration into CM (compare row 1 and 2 in Table 2), bSFS (compare row 3 and 4 in Table 1), bSFS with 0.5 μM AA (compare row 5 and 7 in Table 1), or bSFS with 5 μM AA (compare row 6 and 8 in Table 2) resulted in the generation of higher cell numbers compared to the respective media condition without SB203580. This clearly demonstrates that SB203580 under the conditions tested here has an effect on cell proliferation resulting in higher cell numbers over time.

TABLE 2

Average cell numbers per well observed on day 13 when cell differentiation was performed in respective medium.

| Row # | Media | day 13 cell count per well of a 6-well plate |
|---|---|---|
| 1 | CM | $2.10 \times 10^6$ |
| 2 | CM + 5 μM SB203580 | $3.63 \times 10^6$ |
| 3 | bSFS | $1.18 \times 10^6$ |
| 4 | bSFS + 5 μM SB203580 | $2.08 \times 10^6$ |
| 5 | bSFS + 0.5 μM Acetic Acid (AA) | $1.18 \times 10^6$ |
| 6 | bSFS + 5.0 μM AA | $1.03 \times 10^6$ |
| 7 | bSFS + 5 μM SB203580 + 0.5 μM AA | $1.53 \times 10^6$ |
| 8 | bSFS + 5 μM SB203580 + 5.0 μM AA | $3.38 \times 10^6$ |

Figure 26:
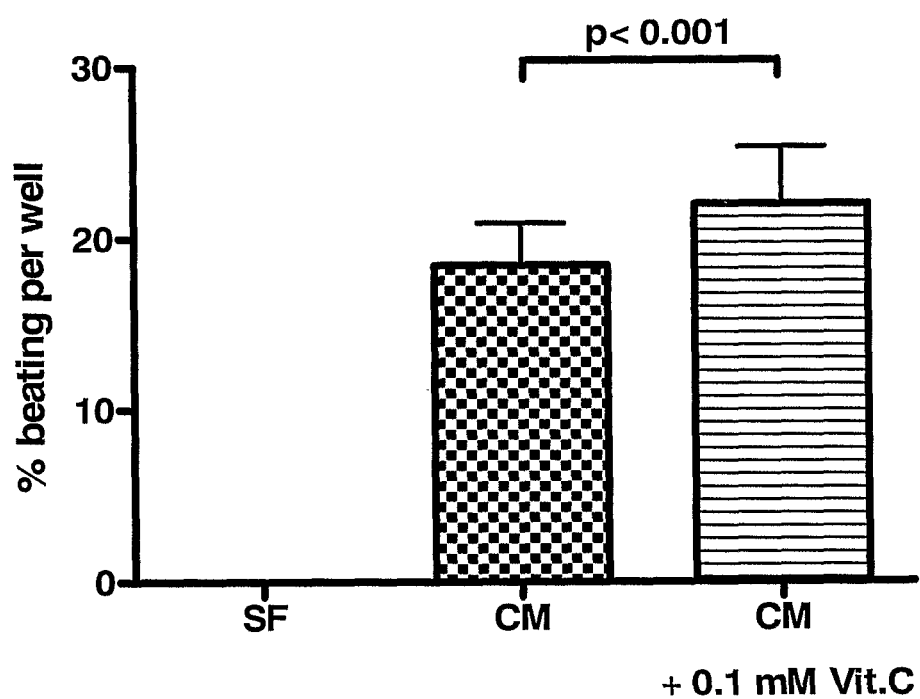
FIG. 26 shows stimulation of cardiomyogenesis in hES-derived EBs by supplementing END2-CM with Vitamin C. END2-CM was supplemented with 0.1 mM Vitamin C during differentiation. EBs were scored for beating foci at days 12.

The addition of Vitamin C to END2-CM may additionally increase the number of beating EBs significantly (FIG. 26).

Passier et al. observed that the addition of Vitamin C to the END2-hES co-culture system increased the number of beating areas by up to 40% (9).

Figure 27:
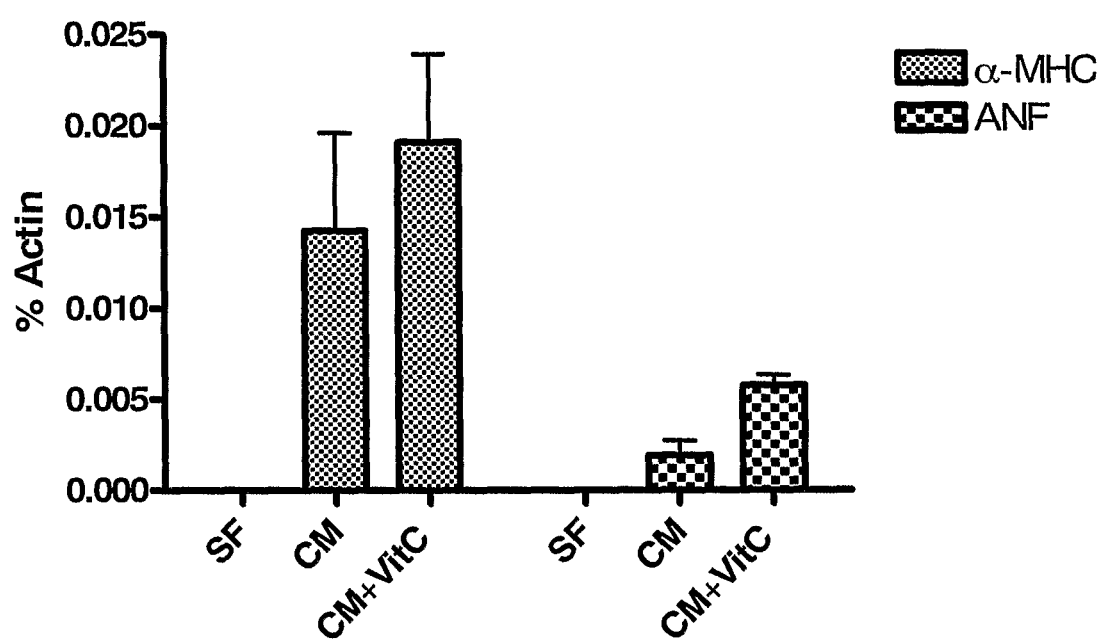
FIG. 27 shows cardiac gene expression in hES-derived EBs after supplementing END2-CM with Vitamin C. END2-CM was supplemented with 0.1 mM Vitamin C during 12 days of differentiation. RNA was extracted and mRNA expression for the cardiac marker genes ANF and α-MHC in SF medium, END2-CM or END2-CM supplemented with Vitamin C analysed by qRT-PCR.

Supplementing END2-CM the same way leads to an increase of up to 20% in the number of beating EBs. The expression of cardiac specific markers like ANF or α-MHC was detectable at day 12 and their expression increased in END2-CM supplemented with Vitamin C (VitC) (FIG. 27). The increased expression level for these two cardiac markers generally reflects the observed increase in beating EBs and therefore cardiomyocytes.

Using the current protocol for cardiac differentiation in suspension cultures we are able to obtain up to ~2×10$^8$ cells in a volume of 200 ml.

Example 10

PGI2 as a Cardiomyocyte Inductive Component of the END2-CM

1. Material and Methods

For hES culture on human feeder cells, see Example 2.

(i) Culture media: basic serum free medium (bSF): DMEM supplemented with 1×MEM non-essential amino acids (Invitrogen), 2 mM L-Glutamine (Invitrogen), 0.1 mM β-mercaptoethanol, with or without Penicillin/Streptomycin (Invitrogen).

Prostaglandin I$_2$ or PGI2-Na [(5Z, 9α, 11α, 13E, 15S)-6, 9-Epoxy-11,15-dihydroxyprosta-5,13-dien-1-oic acid Sodium salt] was obtained from Sigma-Aldrich. It was dissolved in 90% Ethanol at 2 mM as a stock solution and then diluted with PBS before adding to the differentiation medium bSF at a final concentration of 0.2 µM and 2 µM. A medium change with addition of a respective amount of PGI2 was performed at day 3, 6 and 9 after EB formation.

(ii) Immunoassay: To identify molecules that have a cardiomyocyte inductive activity in END2-CM we have determined and quantified the Prostaglandin I$_2$ (or PGI$_2$) content using an EIA assay. END2 cell and MES1 (10) cell conditioned media were collected after day 1, 2, 3 and 4 of conditioning. Measurement of PGI2 concentrations in respective conditioned medium was determined in duplicates using the commercial enzyme immunoassay kit—6 keto Prostaglandin F1α EIA (6 keto PGF1α) kit (Cayman Chemical Co). The assay was performed according to the manual's instruction; DMEM was used as blank and as a diluting solution for the preparation of standards. The assay results were calculated based on the standard curve generated in parallel and using a spreadsheet program provided by Cayman website (www.caymanchem.com/analysis).

For all other methods applied see previous examples.

2. Results

We found that PGI2 was accumulated in END2-CM to much higher concentrations compared to the non-cardiomyocyte inductive, conditioned media collected from MES1 cells (FIG. 28A). PGI2 was added into the defined serum free medium bSF at a final concentration of 0.2 µM and 2 µM and hES differentiation was performed in this medium as well as in SF and END2-CM for 12 days before the percentage of beating EBs and relative expression of cardiac α-MHC expression was tested. We surprisingly found that the addition of PGI2 resulted in a strong induction of cardiomyocyte formation shown by a 3-fold higher percentage of beating EBs and a up to 2-3 fold higher relative expression of the cardiac marker α-MHC (FIG. 28 B-C). The EB beating levels and marker gene expression levels in bSF with PGI2 added at respective concentrations were equivalent or even higher compared to END2-CM. This clearly demonstrates that PGI2 is a cardiomyocyte inductive component of the bioactivity in END2-CM. PGI2 is also inducing cardiomyocyte formation when added into a fully defined medium such as bSF.

REFERENCES

1. Amit, M., Carpenter, M. K., Inokuma, M. S., Chiu, C. P., Harris, C. P., Waknitz, M. A., Itskovitz-Eldor, J., and Thomson, J. A. (2000) *Dev Biol* 227(2), 271-278
2. Reubinoff, B. E., Pera, M. F., Fong, C. Y., Trounson, A., and Bongso, A. (2000) *Nat Biotechnol* 18(4), 399-404
3. Wobus, A. M., Kaomei, G., Shan, J., Wellner, M. C., Rohwedel, J., Ji, G., Fleischmann, B., Katus, H. A., Hescheler, J., and Franz, W. M. (1997) *J Mol Cell Cardiol* 29(6), 1525-1539
4. Pera, M. F., Andrade, J., Houssami, S., Reubinoff, B., Trounson, A., Stanley, E. G., Oostwaard, D. W., and Mummery, C. (2004) *J Cell Sci* 117(Pt 7), 1269-1280
5. Rangappa, S., Fen, C., Lee, E. H., Bongso, A., and Sim, E. K. (2003) *Ann Thorac Surg* 75(3), 775-779
6. Hakuno, D., Fukuda, K., Makino, S., Konishi, F., Tomita, Y., Manabe, T., Suzuki, Y., Umezawa, A., and Ogawa, S. (2002) *Circulation* 105(3), 380-386
7. Xu, C., Police, S., Rao, N., and Carpenter, M. K. (2002) *Circ Res* 91(6), 501-508
8. Kehat, I., Kenyagin-Karsenti, D., Snir, M., Segev, H., Amit, M., Gepstein, A., Livne, E., Binah, O., Itskovitz-Eldor, J., and Gepstein, L. (2001) *J Clin Invest* 108(3), 407-414
9. Passier, R., Oostwaard, D. W., Snapper, J., Kloots, J., Hassink, R. J., Kuijk, E., Roelen, B., de la Riviere, A. B., and Mummery, C. (2005) *Stem Cells* 23(6), 772-780
10. Mummery, C. L., van Achterberg, T. A., van den Eijnden-van Raaij, A. J., van Haaster, L., Willemse, A., de Laat, S. W., and Piersma, A. H. (1991) *Differentiation* 46(1), 51-60
11. Patent application WO 03/010303: Methods of inducing differentiation of stem cells
12. Engel, F. B., Schebesta, M., Duong, M. T., Lu, G., Ren, S., Madwed, J. B., Jiang, H., Wang, Y., and Keating, M. T. (2005) *Genes Dev*
13. Cuenda, A., Rouse, J., Doza, Y. N., Meier, R., Cohen, P., Gallagher, T. F., Young, P. R., and Lee, J. C. (1995) *FEBS Lett* 364(2), 229-233
14. Davidson, S. M., and Morange, M. (2000) *Dev Biol* 218(2), 146-160
15. Wu, X., Ding, S., Ding, Q., Gray, N. S., and Schultz, P. G. (2004) *J Am Chem Soc* 126(6), 1590-1591
16. Costa, M., Dottori, M., Ng, E., Hawes, S. M., Sourris, K., Jamshidi, P., Pera, M. F., Elefanty, A. G., and Stanley, E. G. (2005) *Nat Methods* 2(4), 259-260
17. Mummery, C., Ward-van Oostwaard, D., Doevendans, P., Spijker, R., van den Brink, S., Hassink, R., van der Heyden, M., Opthof, T., Pera, M., de la Riviere, A. B., Passier, R., and Tertoolen, L. (2003) *Circulation* 107(21), 2733-2740
18. Schroeder, M., Niebruegge, S., Werner, A., Willbold, E., Burg, M., Ruediger, M., Field, L. J., Lehmann, J., and Zweigerdt, R. (2005) *Biotechnol Bioeng* 92(7), 920-933
19. Livak, K. J., and Schmittgen, T. D. (2001) *Methods* 25(4), 402-408
20. Amit, M., Shariki, C., Margulets, V., and Itskovitz-Eldor, J. (2004) *Biol Reprod* 70(3), 837-845

21. Bird, S. D., Doevendans, P. A., van Rooijen, M. A., Brutel de la Riviere, A., Hassink, R. J., Passier, R., and Mummery, C. L. (2003) *Cardiovasc Res* 58(2), 423-434
22. Keller, G. (2005) *Genes Dev* 19(10), 1129-1155
23. Cai, J., Chen, J., Liu, Y., Miura, T., Luo, Y., Loring, J. F., Freed, W. J., Rao, M. S., and Zeng, X. (2006) *Stem Cells* 24(3), 516-530
24. Showell, C., Binder, O., and Conlon, F. L. (2004) *Dev Dyn* 229(1), 201-218
25. Saga, Y., Kitajima, S., and Miyagawa-Tomita, S. (2000) *Trends Cardiovasc Med* 10(8), 345-352
26. Ueyama, T., Kasahara, H., Ishiwata, T., Nie, Q., and Izumo, S. (2003) *Mol Cell Biol* 23(24), 9222-9232
27. Leor, J., Patterson, M., Quinones, M. J., Kedes, L. H., and Kloner, R. A. (1996) *Circulation* 94(9 Suppl), II332-II336
28. Small, E. M., and Krieg, P. A. (2004) *Trends Cardiovasc Med* 14(1), 13-18
29. Aouadi, M., Bost, F., Caron, L., Laurent, K., Le Marchand Brustel, Y., and Binetruy, B. (2006) *Stem Cells*
30. Reubinoff, B. E., Itsykson, P., Turetsky, T., Pera, M. F., Reinhartz, E., Itzik, A., and Ben-Hur, T. (2001) *Nat Biotechnol* 19(12), 1134-1140
31. Kubo, A., Shinozaki, K., Shannon, J. M., Kouskoff, V., Kennedy, M., Woo, S., Fehling, H. J., and Keller, G. (2004) *Development* 131(7), 1651-1662

The invention claimed is:

1. A method of inducing or enhancing the induction of differentiation of human pluripotent stem cells into ectoderm or mesoderm, said method comprising culturing the human pluripotent stem cells in the presence of a defined medium that is substantially free of xeno- and serum-components, wherein the defined medium comprises a p38MAP kinase inhibitor chosen from SB203580 and SB202190, or prostaglandin I2 (PGI2).

2. A method according to claim 1 wherein the differentiation is dose dependent on the p38MAP kinase inhibitor or PGI2.

3. A method according to claim 1 wherein the p38MAP kinase inhibitor is SB203580.

4. A method according to claim 3 wherein the SB203580 is present in a range of 0.1-100 μM.

5. A method according to claim 3 wherein the SB203580 is present in a range of 0.1-50 μM.

6. A method according to claim 1 wherein PGI2 is present in a range of 2 nM to 200000 nM.

7. A method according to claim 6 wherein PGI2 is present in a range of 200 nM to 20000 nM.

8. A method according to claim 7 wherein the PGI2 is present in a range of 200 nM to 2000 nM.

9. A method according to any one of claims 3 to 5 wherein the SB203580 is present in a range of 0.5-20 μM.

10. A method according to claim 9 wherein the mesoderm is cardiac mesoderm.

11. A method according to claim 10 wherein the cardiac mesoderm gives rise to a cardiomyocyte.

12. A method according to any one of claims 3 to 7 wherein the SB203580 is present in the range of 10-50 μM.

13. A method according to claim 12 wherein the ectoderm is neural ectoderm.

14. A method according to claim 1 wherein the stem cell is a human ES cell.

15. A method according to claim 1 wherein the medium further comprises at least one additive selected from the group consisting of selenium, transferrin, retinoic acid, ascorbic acid, acetic acid, hydrogen peroxide, bone morphogenetic protein and fibroblast growth factors.

* * * * *